(12) United States Patent
Grimm et al.

(10) Patent No.: US 6,624,342 B1
(45) Date of Patent: Sep. 23, 2003

(54) MANIPULATION OF TOCOPHEROL CONTENT IN TRANSGENIC PLANTS

(75) Inventors: Bernhard Grimm, Gatersleben (DE); Ryouichi Tanaka, Sapporo (JP)

(73) Assignee: Institut fur Pflanzengenetik und Kulturpflanzenforschung (DE)

( * ) Notice: Subject to any disclaimer, the term of this patent is extended or adjusted under 35 U.S.C. 154(b) by 0 days.

(21) Appl. No.: 09/564,367

(22) Filed: Apr. 28, 2000

Related U.S. Application Data

(63) Continuation of application No. PCT/EP98/06851, filed on Oct. 29, 1998.

(30) Foreign Application Priority Data

Oct. 29, 1997 (DE) .......................................... 197 47 739

(51) Int. Cl.[7] .......................... C12N 15/82; C12N 5/04; A01H 5/00
(52) U.S. Cl. ...................... 800/278; 800/298; 800/306; 800/312; 800/317.2; 800/317.4; 800/320; 800/320.1; 800/320.2; 800/320.3; 435/419
(58) Field of Search ................................ 435/419, 468, 435/320.1; 800/278, 281, 282, 298, 306, 12, 317.2, 317.4, 320, 320.1, 320.2, 320.3

(56) References Cited

PUBLICATIONS

Shewmaker et al, "Seed–specific overexpression of phytoene synthase: increase in carotenoids and other metabolic effects", 1999, The Plant Journal vol. 20 No. 4, pp. 401–412.*

Burkhardt et al, Transgenic rice (Oryza sativa) endosperm expressing daffodil (Narcissus pseudonarcissus) phytoene synthase . . . A bioysnthese, 1997, The Plant Journal vol. 11 No. 5, pp. 1071–1078.*

* cited by examiner

*Primary Examiner*—Elizabeth F. McElwain
*Assistant Examiner*—Cynthia Collins
(74) *Attorney, Agent, or Firm*—Schwegman, Lundberg, Woessner & Kluth, P.A.

(57) ABSTRACT

The present invention relates to new nucleic acid sequences, which code for a geranylgeranyl reductase, a method for producing new plants which contain the new DNA sequence and the content of tocopherol and/or chlorophyll of which is altered in comparison to wild-type plants, these new plants, parts and products thereof and plant cells as well as the use of the DNA sequences for the manipulation of tocopherol, chlorophyll and/or vitamin $K_1$ content in transgenic plants, parts and products thereof and plant cells.

31 Claims, 8 Drawing Sheets

```
ATGGCTTCCA TTGCTCTCAA AACTTTCACC GGCCTCCGTC AATCCTCGCC GGAAAACAAT
TCCATTACTC TTTCTAAATC CCTCCCCTTC ACCCAAACCC ACCGTAGGCT CCGAATCAAT
GCTTCCAAAT CCAGCCCAAG AGTCAACGGC CGCAATCTTC GTGTTGCGGT GGTGGGCGGT
GGTCCTGCTG GTGGCGCCGC CGCTGAAACA CTCGCCAAGG GAGGAATTGA AACCTTCTTA
ATCGAACGCA AAATGGACAA CTGCAAACCC TGCGGTGGGG CCATCCCACT TTGCATGGTG
GGAGAATTTG ACCTCCCTTT GGATATCATT GACCGGAAAG TTACAAAGAT GAAGATGATT
TCCCCATCCA ACGTTGCTGT TGATATTGGT CAGACTTTAA AGCCTCACGA GTACATCGGT
ATGGTGCGCC GCGAAGTACT CGATGCTTAC CTCCGTGACC GCGCTGCTGA AGCCGGAGCC
TCTGTTCTCA ACGGCTTGTT CCTCAAAATG GACATGCCCA AAGCTCCCAA CGCACCTTAC
GTCCTTCACT ACACAGCTTA CGACTCCAAA ACTAATGGCG CGGGGGAGAA GCGTACCCTG
GAAGTTGACG CCGTTATCGG CGCTGACGGT GCAAATTCCC GTGTCGCAAA ATCCATAAAC
GCCGGTGACT ACGAGTACGC TATTGCATTC AAGAAAGGA TTAAAATTTC CGATGATAAA
ATGAAGTATT ACGAGAATTT AGCTGAAATG TACGTGGGTG ATGACGTGTC CCCTGATTTT
TACGGGTGGG TTTTCCCCAA ATGTGACCAC GTTGCCGTTG GCACTGGCAC AGTCACCCAC
AAAGCTGACA TCAAAAAATT CCAGCTAGCT ACAAGATTGA GAGCTGATTC CAAAATCACC
GGCGGAAAAA TTATCCGGGT CGAGGCCCAC CCGATTCCAG AACACCCAAG ACCCAGAAGA
TTACAAGACA GAGTTGCATT GGTTGGTGAT GCGGCAGGGT ACGTGACCAA ATGTTCGGGC
GAAGGGATTT ACTTCGCGGC AAAGAGTGGA CGTATGTGTG CTGAAGCAAT TGTTGAAGGG
TCAGAAATGG GAAAAGAAT GGTGGACGAG AGTGATTTGA GGAAGTATTT GGAGAAATGG
GACAAGACTT ATTGGCCAAC GTACAAGGTG CTCATATAT TGCAGAAGGT ATTTTACAGG
TCGAATCCGG CGAGGGAAGC ATTTGTTGAA ATGTGCGCAG ATGAGTATGT GCAGAAGATG
ACATTTGACA GCTATTTGTA CAAGAAAGTA GCACCAGGAA ACCCAATTGA AGACTTGAAG
CTTGCTGTGA ATACCATTGG AAGTTTGGTG AGAGCTAATG CACTAAGAAG GGAAATGGAC
AAGCTCAGTG TATAAGAAGA TTAACAGCAT TAATATTTTC TTGTAATTGA AGGATTTATT
TCTCAAATTA CTCTGTAAAC ACCTTTCATC CTGCCTTTAA TCGGATTTAT GTAACTTCAT
AATTTGAGCT
```

Fig.1

```
  1 Met Ala Ser Ile Ala Leu Lys Thr Phe Thr Gly Leu Arg Gln Ser
 16 Ser Pro Glu Asn Asn Ser Ile Thr Leu Ser Lys Ser Leu Pro Phe
 31 Thr Gln Thr His Arg Arg Leu Arg Ile Asn Ala Ser Lys Ser Ser
 46 Pro Arg Val Asn Gly Arg Asn Leu Arg Val Ala Val Val Gly Gly
 61 Gly Pro Ala Gly Gly Ala Ala Ala Glu Thr Leu Ala Lys Gly Gly
 76 Ile Glu Thr Phe Leu Ile Glu Arg Lys Met Asp Asn Cys Lys Pro
 91 Cys Gly Gly Ala Ile Pro Leu Cys Met Vat Gly Glu Phe Asp Leu
106 Pro Leu Asp Ile Ile Asp Arg Lys Val Thr Lys Met Lys Met Ile
121 Ser Pro Ser Asn Val Ala Vat Asp Ile Gly Gln Thr Leu Lys Pro
136 His Glu Tyr Ile Gly Met Val Arg Arg Glu Val Leu Asp Ala Tyr
151 Leu Arg Asp Arg Ala Ala Glu Ala Gly Ala Ser Val Leu Asn Gly
166 Leu Phe Leu Lys Met Asp Met Pro Lys Ala Pro Asn Ala Pro Tyr
181 Val Leu His Tyr Thr Ala Tyr Asp Ser Lys Thr Asn Gly Ala Gly
196 Glu Lys Arg Thr Leu Glu Val Asp Ala Val Ile Gly Ala Asp Gly
211 Ala Asn Ser Arg Val Ala Lys Ser Ile Asn Ala Gly Asp Tyr Glu
226 Tyr Ala Ile Ala Phe Gln Glu Arg Ile Lys Ile Ser Asp Asp Lys
241 Met Lys Tyr Tyr Glu Asn Leu Ala Glu Met Tyr Val Gly Asp Asp
256 Val Ser Pro Asp Phe Tyr Gly Trp Val Phe Pro Lys Cys Asp His
271 Val Ala Val Gly Thr Gly Thr Val THr His Lys Ala Asp Ile Lys
286 Lys Phe Gln Leu Ala Thr Arg Leu Arg Ala Asp Ser Lys Ile Thr
301 Gly Gly Lys Ile Ile Arg Val Glu Ala His Pro Ile Pro Glu His
316 Pro Arg Pro Arg Arg Leu Gln ASp Arg Val Ala Leu Val Gly Asp
331 Ala Ala Gly Tyr Val Thr Lys Cys Ser Gly Glu Gly Ile Tyr Phe
346 Ala Ala Lys Ser Gly Arg Met Cys Ala Glu Ala Ile Val Glu Gly
361 Ser Glu Met Gly Lys Arg Met Val Asp Glu Ser Asp Leu Arg Lys
376 Tyr Leu Glu Lys Trp Asp Lys Thr Tyr Trp Pro Thr Tyr Lys Val
391 Leu Asp Ile Leu Gln Lys Val Phe Tyr Arg Ser Asn Pro Ala Arg
406 Glu Ala Phe Val Glu Met Cys Ala ASp Glu Tyr Val Gln Lys Met
421 Thr Phe Asp Ser Tyr Leu Tyr Lys Lys Val Ala Pro Gly Asn Pro
436 Ile Glu Asp Leu Lys Leu Ala Val Asn Thr Ile Gly Ser Leu Val
451 Arg Ala Asn Ala Leu Arg Arg Glu Met Asp Lys Leu Ser Val
```

Fig.2

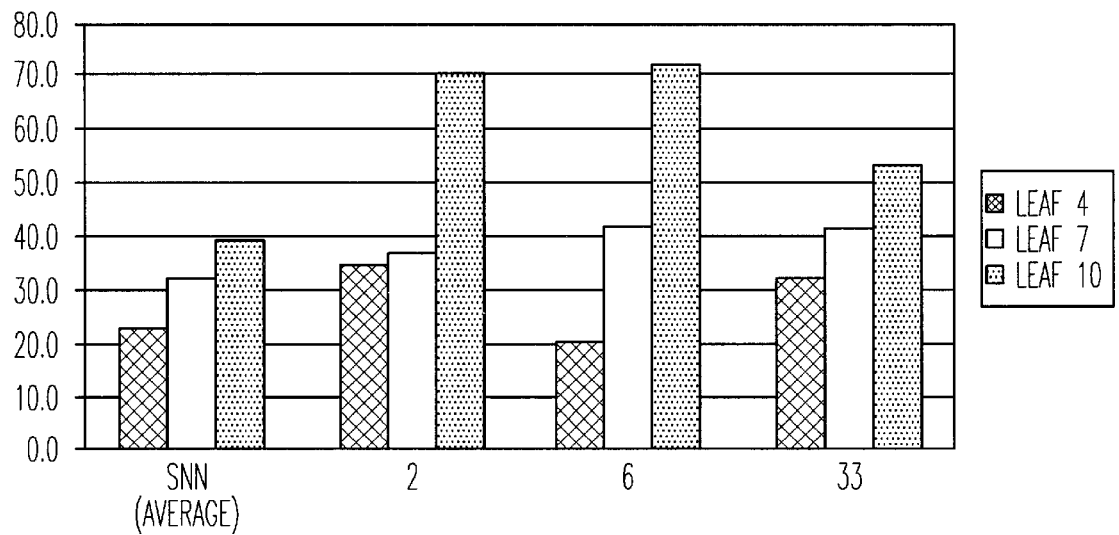
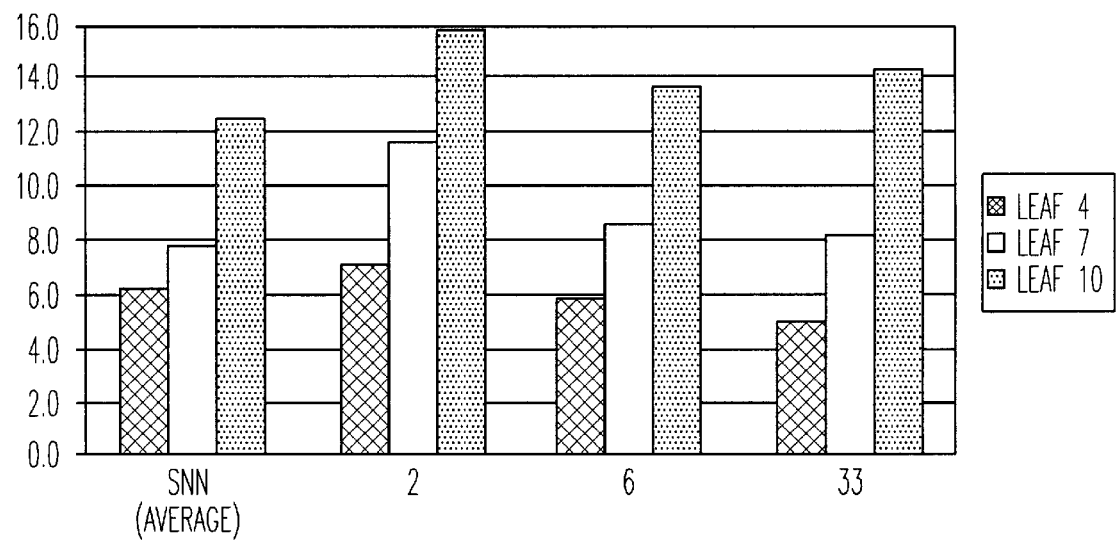
Fig.6

MANIPULATION OF TOCOPHEROL CONTENT IN TRANSGENIC PLANTS

CROSS-REFERENCE TO RELATED APPLICATIONS

This application is a continuation of International Patent Application No. PCT/EP98/06851, filed on Oct. 29, 1998, which in turn is an international filing of German Patent Application No. 19747739.9 filed on Oct. 29, 1997, all of which are incorporated herein by reference.

The present invention relates to novel nucleic acid sequences, which code for a geranylgeranyl reductase, a method for producing novel plants, which contain a novel nucleic acid sequence and the tocopherol and/or chlorophyll content of which is altered in comparison with wild-type plants, these novel plants, parts and products thereof and plant cells as well as the use of the nucleic acid sequences for the manipulation of tocopherol, chlorophyll and/or vitamin $K_1$ content in transgenic plants, parts and products thereof and plant cells.

The diterpene geranylgeranyl pyrophosphate (GGPP) is formed as $C_{20}$-intermediate in the plant isoprenoid metabolism. It results from the addition of one unit isopentenyl pyrophosphate (IPP) to farnesyl pyrophosphate, a $C_{15}$-sesquiterpene. GGPP enters several synthesis pathways of plant secondary metabolism. For example, two molecules of GGPP can be joined "tail to tail" to give $C_{40}$-bodies, the tetraterpenes, generally called carotenoides and to which, for example, the β-carotene belongs. By the addition of further molecules of IPP, GGPP furthermore enters the biosynthesis of polyterpenes, such as rubber and guttapercha.

Further, GGPP can be transformed into other diterpenes, such as phytyl pyrophosphate (PPP). The $C_{20}$-body phytol is an obligatory intermediate in the biosynthesis of the tocopherols (Soll and Schulz (1981) Biochem. Biophys. Res. Commun. 99, 907–912) as well as the synthesis of the chlorophylls (Beale and Weinstein (1990) in: Biosynthesis of Heme and Chlorophyll (Daily H. A., ed.) McGraw Hill, N.Y., 287–391). While the basic structure of all chlorophylls (chlorophyll a, b, c, etc.) is a porphyrin system consisting of four pyrrole rings, to which system the phytol is bound by an ester-like bond through the pyrrole ring IV, the tocopherols are characterised by a structure consisting of homogentisate and a phytol tail.

The group of tocopherols, commonly described as vitamin E, comprises several structurally closely related lipophilic vitamins, viz α-, β-, γ-, δ- und ε-tocopherol, α-tocopherol being the most important in biological terms. The tocopherols can be found in many plant oils, specially rich in tocopherols are the seed oils of soybean, wheat, maize, rice, cotton, lucerne and nuts. Also fruits and vegetables, e.g. raspberries, beans, peas, fennel, pepper etc. contain tocophrols. As far as presently known, tocopherols are exclusively synthesized in plants and photosynthetically active organisms.

Due to their redox potential tocopherols contribute to avoid oxidation of unsaturated fatty acids by air oxygen; α-tocopherol is the most important lipophilic antioxidant in human. It is assumed that due to their function as antioxidative agents the tocopherols contribute to the stabilisation of biological membranes, because the fluidity of the membranes is maintained by the protection of the unsaturated fatty acids of the membrane lipids. Moreover, according to recent observations, regular uptake of relatively high tocopherol doses can counteract the development of arteriosclerosis. Further positive physiological properties and influences of tocopherols have been described, such as delay of late damages associated with diabetes, reduction of the risk of cataract development, reduction of oxidative stress in smokers, anticarcinogenic effects, protective effects against skin damages such as erythremes and skin aging etc.

Due to their oxidation inhibiting properties the tocopherols are not only used in food technology applications, but also employed in paintings based on natural oils, in deodorants and other cosmetics, such as sun protection agents, skin care agents, lip sticks etc. In such applications tocopherol compounds like tocopheryl acetate and succinate are usual application forms for the use as vitamin E, in circulation promoting and lipid reducing agents and as food additive in veterinary applications.

In the biosynthesis of tocopherols, in particular in the biosynthesis of α-tocopherol, phytyl pyrophosphate is believed to be the limiting factor. Previous studies indicate that PPP is formed from GGPP by sequential hydrogenation of the isoprenoid group, during which reaction dihydro-GGPP and tetrahydro-GGPP are formed as intermediates (GGPP->dihydro-GGPP->tetrahydro-GGPP->PPP; cf., for example, Bollivar et al. (1994) Biochemistry 33, 12763–12768).

The stepwise hydrogenation of GGPP to PPP is, as presently assumed, catalyzed by the enzyme geranylgeranyl reductase (GGPP reductase, also called geranylgeranyl pyrophosphate hydrogenase and GGPP hydrogenase), which is coded in plants in the gene Chl P. The enzyme geranylgeranyl reductase belongs to the isoprenoid metabolism and functions for two metabolic pathways: the tocoperol biosynthesis and the chlorophyll biosynthesis.

The essential role of this enzyme has been shown for the first time for the biosynthesis of chlorophyll (Benz et al. (1980) Plant Sci. Lett. 19, 225–230; Soll and Schultz (1981) Biochem. Biophys. Res. Commun. 99, 907–912; Schoch et al. (1977) Z. Pflanzenphysiol. 83, 427–436). The final step in chlorophyll biosynthesis is the esterification of chlorophyllide, which may take place with phytyl pyrophosphate as well as with geranylgeranyl pyrophosphate. In systematic studies of *Rhodobacter capsulatus* mutants it could be demonstrated that bacteriochlorophyllide is esterified with GGPP in a first step and that subsequently esterified chlorophyll-GG is hydrogenated (Katz et al. (1972) J. Am. Chem. Soc. 94, 7938–7939). In higher plants, phytyl chlorophyll (chlorophyll-P) can be found for the most part (Rüdiger and Schoch (1991) In: Chlorophylls (Scheer, H., Ed.) pp. 451–464, CRC Press, Boca Raton, Fla., USA). So far it has not been elucidated yet, which substrates are involved in the reductase reaction in plants. Presently, it is assumed that the plant enyzme geranylgeranyl reductase is able to transform chlorophyll-GG into chlorophyll-P (Schoch et al. (1978) Z. Pflanzenphysiol. 83, 427–436) as well as to hydrogenate GGPP to PPP, which is then subsequently joined to chlorophyllide (Soll et al. (1983) Plant Physiol. 71, 849–854).

GGPP serves as the substrate for the synthesis pathways of tocopherol and phyllochinone in the chloroplast outer membranes and for chlorophyll synthesis in the thylakoid membranes. The reduction of GGPP to PPP has been described for the first time 1983 by Soll et al. (Plant. Physiol. (1983) 71, 849–854). However, until now the isolation and characterisation of nuclic acid sequences, which code for the plant enzyme and which can be used for the manipulation of tocopherol content in transgenic plants, was unsuccessful.

The essential role of geranylgeranyl reductase in tocopherol and chlorophyll metabolism makes this enzyme a particular valuable instrument for molecular biotechnology. By means of molecular biological techniques such as the transfer of DNA sequences coding for geranylgeranyl reductase, it should be possible to achieve alterations in tocopherol and/or chlorophyll biosynthesis performance in plants. By this way it would, for example, become possible to produce transgenic plants having an increased or reduced tocopherol content. Such transgenic plants and parts, cells and/or products thereof could subsequently be used as food and feed and in general as production center for tocopherol, for use in chemical, pharmaceutical and cosmetic industrial applications.

Further, there is reason to expect that plants which exhibit an increased content of antioxidative tocopherols, in comparison with wild-type plants, also show increased tolerance against stress conditions, in particular against oxidative stress.

It is therefore an object of the invention to provide new nucleic acid sequences, with the help of which the content of tocopherol can be manipulated in plants, plant cells, plant parts and/or plant products.

Further it is an important object of the invention to provide transgenic plants, plant cells, plant products and plant parts having an altered tocopherol content compared to wild-type plants.

It is a further object of the invention to show possible ways how to use the DNA sequences according to the invention, their gene products as well as the transgenic plants according to the invention for plant breeding practice.

Further objects of the invention will be seen from the following description. These problems are solved by the subject-matters of the independent claims, particularly based on the provision of the DNA sequences according to the invention, the gene products of which are directly involved in tocopherol biosynthesis, and the transfer of these DNA sequences to plants, which results in an altered tocopherol content.

The present invention thus relates to DNA sequences which code for proteins having biological activity of a geranylgeranyl reductase (also called geranylgeranyl pyrophosphate hydrogenase) or for a biologically active fragment thereof. In connection with this invention, biologically active fragment means that the mediated biological activity is sufficient to influence the tocopherol content. The invention relates in particular to DNA sequences which are isolated from plants and which code for proteins having enyzmatic activity of a geranylgeranyl reductase or a biologically active fragment thereof. Particularly preferred is the DNA sequence shown in SEQ ID NO:1 (see also FIG. 1).

Further, the invention relates to alleles and derivatives of the DNA sequences according to the invention, which code for a protein having biological activity of a geranylgeranyl reductase, especially nuclic acid molecules, the sequences of which differ from the DNA sequences according to the invention due to the degeneracy of the genetic code and which code for a protein or a fragment thereof having the biological activity of a geranylgeranyl reductase.

Furthermore, the invention relates to nucleic acid molecules which comprise the DNA sequences according to the invention or which originate from the sequences according to the invention by naturally occurring or by gene technological or chemical processes and synthesis methods or which are deduced therefrom. The nucleic acid molecules can be any form of nucleic acid, such as DNA or RNA molecules, cDNA, genomic DNA, mRNA, etc.

The invention also relates to nucleic acid molecules wherein the DNA sequences according to the invention are combined with regulatory elements that provide transcription and, if desired, translation in the plant cell.

Thus, it is possible to express the DNA sequences according to the invention in plant cells, for example, under control of constitutive, but also under control of inducible or tissue-specific or developmental specific regulatory elements, particularly promoters. While, for example, the use of an inducible promoter makes it possible to achieve specifically triggered expression of the DNA sequences according to the invention in plant cells, the use of tissue-specific, for example seed-specific, promoters provides the possibility to modify the tocopherol content in specific tissues, for example, in seed tissue. Therefore, in a preferred embodiment of the invention, the DNA sequences according to the invention are in combination with tissue-specific promoters, particularly in combination with seed-specific promoters.

The invention further relates to proteins having the biological activity of a geranylgeranyl reductase or active fragments thereof, which are encoded by a DNA sequence according to the invention or a nucleic acid molecule according to the invention. Preferably, the protein is a plant geranylgeranyl reductase, preferably from *Nicotiana tabacum,* especially preferred is a protein having the amino acid sequence shown in SEQ ID NO:2 (cf. also FIG. 2), or an active fragment thereof.

It is a further object of the invention to provide vectors and microorganisms, the use of which makes it possible to produce new plants wherein an altered tocopherol content can be achieved. This problem is solved by the provision of the vectors and microorganisms according to the invention, which comprise nucleic acid sequences that code for enzymes having the activity of a geranylgeranyl reductase.

The present invention, thus, also relates to vectors, in particular plasmids, cosmids, viruses, bacteriophages and other vectors customarily used in genetic engineering, which comprise the nucleic acid molecules according to the invention, as described above, and which, if desired, can be used for the transfer of the nucleic acid molecules according to the invention to plants and plant cells.

The invention also relates to transformed microorganisms, such as bacteria, viruses, fungi, yeasts, etc., which contain the nucleic acid sequences according to the invention.

In a preferred embodiment the nucleic acid molecules, contained in the vectors, are combined with regulatory elements that provide transcription and, if desired, translation in procaryotic and eucaryotic cells.

If desired, the nucleic acid sequences according to the invention may be supplemented by enhancer sequences or other regulatory sequences. These regulatory sequences comprise, e.g. also signal sequences which provide the transport of the gene product to a certain cell compartment.

It is also an object of the invention to provide new plants, plant cells, plant parts or plant products exhibiting altered tocopherol content, which may be linked to modified chlorophyll biosynthesis performance, compared to wild-type plants.

These problems are solved by the transfer of the nucleic acid molecules according to the invention and their expression in plants. By providing the nucleic acid molecules according to the invention, it is now possible to manipulate plant cells by gene technology methods in such a way that they exhibit new or altered geranylgeranyl reductase activity, in comparison with wild-type cells, and as a consequence show an altered tocopherol biosynthesis performance and modified tocopherol content.

In a preferred embodiment, the invention relates to plants and plant cells and parts thereof, wherein the tocopherol content is increased, in comparison with wild-type plants, due to the presence and expression of the nucleic acid molecules according to the invention.

The invention also relates to plants wherein the transfer of the nucleic acid molecules according to the invention leads to a reduction of tocopherol and/or chlorophyll content. A reduced tocopherol and/or chlorophyll biosynthesis productivity may, for example, be achieved by the transfer of antisense constructs or other suppression mechanisms, such as co-suppression.

Further, the invention relates to transgenic plant cells and plants comprising such plant cells, and parts and products thereof, wherein the new nucleic acid molecules are integrated into the plant genome. The invention also relates to plants, in the cells of which the nucleic acid sequence according to the invention is present in self-replicating form, i.e. the plant cell contains the foreign DNA on an autonomous nucleic acid molecule.

The plants, which are transformed with the nucleic acid molecules according to the invention and wherein an altered amount of tocopherol and/or chlorophyll is synthesised due to the transfer of such molecule, can, in principle, be any plant. Preferably, the plant is a monocotyle or dicotyle useful plant. Examples of monocotyl plants are plants which belong to the genus of avena (oat), triticum (wheat), secale (rye), hordeum (barley), oryza (rice), panicum, pennisetum, setaria, sorghum (millet), zea (maize). Dicotyl useful plants are, inter alia, leguminous plants, such as legumes and especially alfalfa, soy bean, rape, tomato, sugar beet, potato, ornamental plants, trees. Other useful plants can be, for example, fruit-bearing plants (particularly apples, pears, cherries, grapes, citrus fruits, pineapples and bananas), oil palms, tea, cocoa and coffee shrubs, tobacco, sisal, cotton, flax, sunflower as well as medical plants and pasture grasses, forage cereals and feed plants. Special preference is given to grains, cereals, wheat, rye, oat, barley, rice, maize and millet, forage cereals, sugar beet, rape, soy bean, tomato, potato, sweet grasses, feed grasses, forage grasses and clover. It is self-evident that the invention particularly relates to common food and forage plants. In this context, in addition to the plants already mentioned, peanut, lentil, forage bean (Ackerbohne), mangel, buckwheat, carrot, topinambur, Brassica (rapa, oleifera, napus, rapifera), white mustard and swede are to be mentioned.

Furthermore, the invention relates to propagation material of plants according to the invention, such as seeds, fruits, cuttings, tubers, root stocks, etc., whereby this propagation material may contain the above described transgenic plant cells, as well as parts of such plants, such as protoplasts, plant cells and calli.

The invention further relates to plant cells which, due to the presence and, if desired, expression of the nucleic acid molecules according to the invention, have an altered content of vitamin $K_1$ in comparison with plant cells which do not contain the nucleic acid molecules. The lipophilic vitamin $K_1$, which is present in particular in plants, plays an essential role in the formation of coagulation factors; lack of vitamin $K_1$ leads to a reduction in blood coagulation, which is why vitamin $K_1$ is also called anti-haemorrhagic or coagulation vitamin. Since the expression of the nucleic acid molecules according to the invention results in an altered geranylgeranyl reductase activity and, thus, in an altered PPP-synthesis performance, and in view of the fact that phylloquinone, called vitamin $K_1$, as the tocopherols, comprises one unit of phytol, the invention also relates to such plant cells and plants which exhibit an altered vitamin $K_1$ content, alone or in combination with an altered tocopherol content.

In a preferred embodiment, the invention relates to transgenic plant cells and plants and parts and products thereof, which have an altered tocopherol content, in comparison with non-transformed cells, due to the presence and, if desired, expression of a DNA sequence coding for a plant geranylgeranyl reductase. Preferably, the DNA sequence, contained within the plant cells, is a sequence coding for geranylgeranyl reductase which is isolated from tobacco. Specially preferred is a DNA sequence as shown in SEQ ID NO:1 (cf. also FIG. 1). In a particularly preferred embodiment the DNA sequences according to the invention encode for a geranylgeranyl reductase pre-enzyme, comprising a transit sequence for translocation into plastids.

The invention further relates to plants wherein, in addition to the chl P gene, a gene for hydroxyphenyl pyruvate dioxygenase (HPD) is expressed. The enzyme HPD catalyses the reaction of 4-hydroxyphenylpyruvate into homogentisate, which, as mentioned above, represents the second precursor of the tocopherols, besides phytol. The enzyme HPD as well as its role within the plant isoprenoid metabolism are described, inter alia, in Norris et al. (1995) The Plant Cell 7, 2139–2149.

By co-expression, preferably over-expression, of sequences which code for geranlygeranyl reductase and HPD, respectively, the tocopherol content in transgenic plants can be further increased in comparison with plants which only contain the sequences according to the invention coding for chl P.

In a further embodiment, the invention relates to host cells, particularly procaryotic or eucaryotic cells, which have been transformed or infected with a nucleic acid molecule or a vector, as described above, and cells which originate from such host cells and which contain the described nucleic acid molecules or vectors. The host cells can, e.g., be bacteria, algae, yeast and fungus cells as well as plant or animal cells. The invention also relates to such host cells which not only contain the nucleic acid molecules according to the invention, but further contain one or more nucleic acid molecules, transferred by gene technology or naturally, which carry the genetic information for enzymes involved in the biosynthesis of tocopherol, chlorophyll and/or vitamin $K_1$.

It is a further object of the present invention to provide processes for producing plant cells and plants which exhibit altered tocopherol content.

This problem is solved through processes by means of which it is possible to produce new plants and plant cells which show an altered tocopherol content due to the transfer of nucleic acid molecules coding for geranylgeranyl reductase.

Furthermore, this problem is solved through processes by means of which it is possible to produce new plant cells and plants, which, due to co-transfer of nucleic acid molecules coding for geranylgeranyl reductase and nucleic acid molecules coding for HPD or the transfer of nucleic acid molecules coding for geranylgeranyl reductase and for HPD, show an altered tocopherol content in comparison with wild-type plants.

For the production of such new plant cells and plants several different methods can be applied. On the one hand, plants and plant cells can be modified by conventional gene technological transformation methods in such a way that the new nucleic acid molecules are integrated into the plant genome, which means that stable transformants are produced. On the other hand, the nucleic acid molecules according to the invention, the presence and, if desired, expression of which results in altered tocopherol biosynthesis performance, can also be introduced into the plant cell or plant as self-replicating system. For instance, the nucleic acid molecules according to the invention may be contained in a virus that gets in contact with the plant or plant cell.

According to the invention, plant cells which, due to the expression of a nucleic acid sequence according to the invention, show an altered tocopherol content, are produced by a method which includes the following steps:

a) Manufacture of an expression cassette, comprising the following DNA sequences:
  a promoter that provides transcription in plant cells;
  at least one nucleic acid sequence that codes for a protein or a fragment having enzymatic activity of a geranylgeranyl reductase, whereby the nucleic acid sequence is linked to the 3' end of the promoter in sense orientation; and
  if desired, a termination signal for transcription termination and addition of a poly-A-tail to the respective transcript, wherein the termination signal is linked to the 3' end of the coding region;
b) transformation of plant cells with the expression cassette produced in step a);
c) regeneration of transgenic plants and, if desired, propagation of the plants.

As an alternative, the one or more nucleic acid sequences according to the invention can be introduced into the plant cell or plant as self-replicating system.

In a further alternative, step a) of the above method may be modified in such a way that the at least one nucleic acid sequence according to the invention, which codes for a protein or a fragment having enzymatic activity of a geranylgeranyl reductase, is linked to the 3' end of the promoter in antisense orientation.

It is a further object of the invention to show advantageous applications of the nucleic acid sequences according to the invention as well as of the nucleic acid molecules containing these nucleic acid sequences.

This problem is solved by the uses according to the invention of the new DNA molecules for the production of plant cells and plants which exhibit an altered, preferably increased, tocopherol content in comparison to wild-type cells and wild-type plants.

Further, the invention relates to the use of the nucleic acid sequences according to the invention for the production of plants which show an altered chlorophyll content.

Moreover, the invention relates to the use of the nucleic acid sequences according to the invention for the production of plants which show an altered, preferably increased, content of vitamin $K_1$.

It is a further object of the invention to show possible uses of the plants according to the invention and cells, parts and products thereof.

The invention particularly relates to the use of the plants according to the invention as forage and/or food plant. Depending on the achieved increase in vitamin E and/oder $K_1$ content in the transgenic useful plant and products and parts thereof, it may be possible to reduce the amount of respective vitamins, particularly of vitamin E, which otherwise is usually admixed to the feed/food and which is often also required. Under certain circumstances, conventional supplement with vitamins may become superfluous. Aside from this the invention relates in general to an enhancement of the nutritional value of useful plants by increasing the content of tocopherols and/or phyllochinone.

Further, the invention relates to the use of the plant cells, plants, parts and products thereof according to the invention as production sites for vitamin E and/or vitamin $K_1$. Apart from their application due to their vitamin characteristics, for example in dietetic and pharmaceutical products, cosmetics, skin care products, generally for vitamin E supplement, etc., tocopherols are also applied as antioxidants in chemical products such as lipids and oils. The plants according to the invention, thus, represent an important source for the production of tocopherols and/or vitamin $K_1$ in a broad spectrum of commercial purposes.

The invention further relates to the use of the nucleic acid sequences according to the invention in combination with seed-specific promoters for the production of plants, wherein particularly seed tissue exhibits an altered, preferably increased, tocopherol content. In a preferred embodiment of the invention, the nucleic acid sequences according to the invention are used in combination with the USP (Bäumlein et al. (1991) Mol. Gen. Genet. 225, 459–467) or the hordein promoter (Brandt et al. (1985) Carlsberg Res. Commun. 50, 333–345).

The mentioned promoters, particularly seed-specific promoters, are especially useful for specific reduction of the tocopherol and chlorophyll content in transgenic seeds by use of the DNA sequences according to the invention in connection with the antisense approach.

Further, the invention relates to the use of a geranylgeranyl reductase gene for producing an altered tocopherol content in plants.

Moreover, the invention relates to the use of a protein having enzymatic activity of a geranylgeranyl reductase in order to achieve an altered tocopherol content in plants.

Further, the invention relates to the use of the nucleic acid molecules according to the invention, of the proteins according to the invention having geranylgeranyl reductase activity and/or of the transgenic plants and host cells according to the invention having new or altered geranylgeranyl reductase activity for the identification of new herbicidal substances for plant protection. Due to the key role of geranylgeranyl reductase within the chlorophyll and tocopherol biosynthesis, the DNA sequences according to the invention and the proteins encoded thereby are an extremely valuable target for herbicide research.

For example, the proteins according to the invention having enzymatic geranylgeranyl reductase activity can be used for X-ray structure analysis, NMR spectroscopy, molecular modelling and drug design, in order to identify or synthesise inhibitors or effectors of geranylgeranyl reductase and thus potential herbicides, on the basis of the data and knowledge obtained by means of these techniques.

The invention further relates to the use of the nucleic acid sequences according to the invention for the production of herbicide tolerant plants. Sequences coding for geranlygeranyl reductase can be modified by means of standard techniques, or can be supplemented by new sequence elements, and subsequently transferred to plant cells. The transfer of sequences deduced from the sequences according to the invention can, e.g. be used to modify the properties of plants in such a way that more or less functionally active geranylgeranyl reductase or a variant of the geranylgeranyl reductase having altered characteristics is synthesised in the transgenic plant or that the expression level of the chl P gene, present in the transgenic plant, is reduced. As a consequence, by increasing the CHL P activity an increase in the tolerance against herbicides which block chlorophyll biosynthesis, can be achieved. Similarly, e.g. the expression of modified geranylgeranyl reductase genes in transgenic plant cells can be linked to an increase in the tolerance against herbicides.

Further, the invention relates to the use of the nucleic acid sequences according to the invention or of a protein encoded thereby for the production of antibodies.

Thus, the present invention comprises any possible use of the nucleic acid molecules according to the invention, the presence and, if desired, the expression of which in plants causes an alteration in tocopherol content and/or chlorophyll content, as any possible uses of the proteins according to the invention and fragments thereof, the enzymatic activity of which leads to such alteration.

In principle, any promoter functional in the plant of choice can be used, which fulfils the prerequisite that expression controlled by said promoter leads to an altered tocopherol synthesis capacity. In view of the use of the transgenic plants as food and/or forage plants, promoters which provide seed-specific expression are particularly useful in this respect. Examples for such promoters are the USP promoter, the hordein promoter and the napine promoter.

In case such promoters are not already known or not yet available, the strategy and methods for the isolation of such promoters are known to the person skilled in the art. In general, in a first step poly(A)$^+$ RNA is isolated from seed tissue and a cDNA library is established. In a second step, with the help of cDNA clones based on poly(A)$^+$ RNA molecules originating from a non-seed tissue, those clones are identified by hybridization from the first library, whose corresponding poly(A)$^+$ RNA molecules are expressed only in seed tissue. Subsequently, promoters are isolated with the help of cDNAs identified in this manner, which can then be used in order to control expression of the coding nucleic acid sequences described herein. Likewise, other tissue-specific or developmental specific promoters or promoters which can be induced by abiotic stimuli can be isolated and used according to the invention.

Alternatively it may be desired that the plant shows an altered, preferably increased, tocopherol content in several sections or organs, due to expression of the nucleic acid molecules according to the invention. In this case, the use of a constitutive promoter, for example, the use of the 35S RNA promoter from cauliflower mosaic virus may be desirable.

The invention also comprises nucleic acid molecules that code for proteins having biological activity of a geranylgeranyl reductase or biologically active fragments thereof, and which hybridise to the nucleic acid molecules described above. In the context of this invention "biologically active fragment" means in general that the fragment is sufficient for causing an alteration in tocopherol content. The term "hybridisation" means in the context of this invention a hybridisation under conventional hybridisation conditions, preferably under stringent conditions, as e.g. described in Sambrook et al. (1989) Molecular Cloning: A Laboratory Manual, 2nd Edition, Cold Spring Harbor Laboratory Press, Cold Spring Harbor, N.Y.

Nucleic acid molecules that hybridise with the molecules according to the invention, may be isolated, e.g. from genomic or cDNA libraries.

Identification and isolation of such nucleic acid molecules can be carried out using the nucleic acid molecules or parts of these molecules or the reverse complements of these molecules, e.g. by hybridisation according to standard techniques (see, for example, Sambrook et al., supra). For identification and isolation of such nucleic acid molecules, also such sequences can be used which are deduced from the DNA sequences according to the invention, for example degenerated oligonucleotide primers.

Thus, the invention also comprises the use of a DNA sequence according to the invention or fragments thereof for the identification and isolation of homologous sequences from plants or other organisms.

For instance, nucleic acid molecules which display exactly or essentially the nucleic acid sequences described above or fragments of these sequences can be used as hybridisation probe. The fragments used as hybridisation probe can also be synthetic fragments produced with the help of customary synthesis techniques and the sequence of which basically corresponds with that of a nucleic acid molecule according to the invention. Once genes that hybridise with the nucleic acid sequences according to the invention have been identified and isolated, it is necessary to determine their sequence and to analyse the properties of the proteins encoded by these sequences. To do so, a number of molecular biological, biochemical and biotechnological standard methods are available to the person skilled in the art.

The molecules that hybridise with the nucleic acid molecules according to the invention include also fragments, derivatives and allelic variants of the above-described DNA molecules that code for a geranylgeranyl reductase or a biologically, i.e. enzymatically, active fragment thereof. Fragment means in this respect fragments or regions of the nucleic acid molecules which are sufficiently long to code for a polypeptide or protein having enzymatic activity of a geranylgeranyl reductase or a comparable enzymatic activity, which is able to cause an altered tocopherol content. The term "derivative" means in this context that the sequences of these molecules are distinguishable from the sequences of the above-described nucleic acid molecules in one or several positions and show a great extent of homology with these sequences. Homology in this connection means a sequence identity of at least 40%, especially an identity of at least 60%, preferably above 80%, and especially preferably above 90%. The deviations from the above-described nucleic acid molecules can be due to deletion, addition, substitution, insertion or recombination.

Homology means further that there is functional and/or structural equivalence between the nucleic acid molecules in question or between the proteins encoded thereby. With respect to the nucleic acid molecules which are homologous with the above-described molecules and which represent derivatives of these molecules, it concerns usually variants of these molecules that represent modifications which perform the same biological function. These may concern naturally occurring variations, e.g. sequences from other organisms, or mutations, whereby these modifications can have occurred naturally or were introduced through specific mutagenesis. Furthermore, the variations may concern synthetically produced sequences. With respect to the allelic variants, these may occur naturally as well as be synthetically produced variants, or variants produced by recombinant DNA technology.

Usually the proteins encoded by the different variants and derivatives of the nucleic acid molecules according to the invention have common characteristics. Such characteristics are e.g. enzyme activity, molecular weight, immunological reactivity, conformation, etc. Further common characteristics may be physical properties, e.g. migration pattern in gel electrophoresis, chromatographic characteristics, sedimentation coefficients, solubility, spectroscopic properties, stability, pH optimum, temperature optimum, etc. Further, of course, the reactions catalysed by the proteins may have common or similar features.

To prepare the introduction of foreign genes into higher plants, a variety of cloning vectors are available which contain an origin of replication active in *E. coli* and a marker gene for the selection of transformed bacteria cells. Examples of such vectors are pBR322, pUC series, M13mp series, pACYC184, etc. The desired sequence can be inserted into the vector at a suitable restriction site. The plasmid obtained is used for the transformation of *E. coli* cells. Transformed *E. coli* cells are cultured in a suitable medium and subsequently harvested and lysed. The plasmid is recovered. Usually, restriction mapping, gel electrophoresis and other biochemical, molecular biological methods are applied as analysing methods to characterise the recovered plasmid DNA. After each manipulation the plasmid DNA can be digested and the obtained DNA fragments can be linked with other DNA sequences. Each plasmid DNA sequence can be cloned in the same or other plasmids.

For introducing DNA into a plant host cell many well known methods are available and the skilled person can easily determine and select the respectively suitable procedure. These techniques include the transformation of plant cells with T-DNA by using *Agrobacterium tumefaciens* or *Agrobacterium rhizogenes* as transformation means, fusion of protoplasts, direct gene transfer of isolated DNA into protoplasts, microinjection and electroporation of DNA, introduction of DNA by means of biolistic methods and other possibilities.

When injecting and electroporating DNA into plant cells no specific demands per se are made on the plasmids used. The same appplies to direct gene transfer. Here, simple plasmids such as pUC-derivatives, can often be used. If however, whole intact plants are to be regnerated from cells transformed in this way, the presence of a selectable marker gene is usually required. The skilled person is familiar with custamary selection markers, and he can easily select an appropriate marker.

Depending on the method chosen for the introduction of the gene(s) of interest, additional DNA sequences may be required. If, for example, the Ti or Ri plasmid is used for transformation of the plant cell, at least the right border, but frequently both the right and left boader, of the T-DNA contained in the Ti and Ri plasmid must be combined with the gene to be introduced as flanking regions.

If agrobacteria are used for transformation, the DNA to be introduced has to be clones into special plasmids, viz into an intermediary or a binary vector. Due to sequences which are homologous with sequences in the T-DNA, the intermediary vectors can be integrated in the Ti or Ri plasmid of agrobacteria by homologous recombination. In addition, the latter contains the vir region required for the transfer of the T-DNA. Intermediary vectors cannot replicate in agrobacteria. The intermediary vector can be transferred to agrobacteria *Agrobacterium tumefaciens* by means of a helper plasmids (conjugation). Binary vectors can replicate in *E. coli* as well as in agrobacteria. They contain a selection marker gene and a linker or polylinker framed by the right and left border regions of the T-DNA. These vectors can be directly transformed into agrobacteria (Holsters et al.(1978) Molecular and General Genetics 163, 181–187). The agrobacterium which serves as host cell shall contain a plasmid carrying the vir region. The vir region is required for the transfer of the T-DNA to the plant cell. Additional T-DNA may be present. The agrobacterium transformed in the manner described is used for the transformation of plant cells.

The use of T-DNA for the transformation of plant cells has been thoroughly studied and is adequately described in EP 120 515; Hoekema in: The Binary Plant Vector System, Offsetdrokkerij Kanters B. V., Alblasserdam (1985) Chapter V; Fraley et al. (1993) Crit. Rev. Plant. Sci., 4, 1–46 and An et al. (1985) EMBO J. 4, 277–287.

For the transfer of the DNA to the plant cell, plant explantates can be appropriately cultivated with *Agrobacterium tumefaciens* or *Agrobacterium rhizogenes*. Out of the infected plant material (e.g. leaves, leaf pieces, stem segments, rootes, but also protoplasts or plant cells cultivated in suspension cultures) whole plants can be regenerated in a suitable medium which can contain antibiotics or biocides for the selection of transformed cells. The regeneration of plants is carried out according to customary regeneration methods by using conventional nutrient media. Plants obtained in the above-described manner can then be examined for the presence of the introduced DNA. Other possibilities for introducing foreign DNA by applying the biolistic method or through protoplast transformation are known (see, e.g. Wilmitzer L (1993) Transgenic Plants, in: Biotechnology, A Multi-Volume Comprehensive Treatise (H. J. Rehm, G. Reed, A. Pühler, P. Stadler, eds.) Vol. 2, 627–659, V. C. H. Weinheim—New York, Basel— Cambridge).

While the transformation of dicotyle plants via Ti plasmid vector systems with the help of *Agrobacterium tumefaciens* is well established, recent studies indicate that also monocotyle plants can be transformed via Agrobacterium-based vectors (Chan et al. (1993) Plant Mol. Biol. 22, 491–506; Hiei et al. (1994) Plant J. 6, 271–282; Deng et al. (1990) Science in China 33, 28–34; Wilmink et al. (1992) Plant Cell Reports 11, 67–80; May et al. (1995) Bio/Technology 13, 486–492; Conner and Domiss (1992) Int. J. Plant Sci. 153, 550–555; Ritchie et al. (1993) Transgenic Res. 2, 252–265).

Alternative systems for the transformation of monocotyle plants are transformations by means of the biolistic approach (Wan and Lemaux (1994) Plant Physiol. 104, 37–48; Vasil et al. (1993) Bio/Technology 11, 1553–1558; Ritala et al. (1990) Tehor. Appl. Genet. 79, 625–631; Altpeter et al. (1996) Plant Cell Reports 16, 12–17), transformation of protoplasts, electroporation of partially permeabilised cells and the introduction of DNA by means of glass fibres.

The transformation of maize is specifically described several times in the literature (cf. e.g. WO 95/06128, EP 0 513 849; EP 0 465 875; Fromm et al. (1990) Biotechnology 8, 833–844; Gordon-Kamm et al. (1990) Plant Cell 2, 603–618; Koziel et al. (1993) Biotechnology 11, 194–200). EP 292 435 describes a process by means of which, starting from mucusless friable granulous maize callus, fertile plants can be obtained. Shillito et al. ((1989) Bio/Technology 7, 581) have observed in this context that it is further necessary for the generation of fertile plants to start from a callus culture from which a dividing protoplast culture having the ability to regenerate to plants can be obtained. After an in vitro cultivating period of seven to eight months, Shillito et al. obtain plants which are able to produce viable progeny.

Prioli and Sondahl ((1989) Bio/Technology 7, 589) describe the regeneration and the production of fertile plants from maize protoplasts, the cateto maize inbreeding line Cat 100-1. The authors assume that the regeneration of fertile plants from protoplasts depends on a number of different factors, such as the genotype, the physiological condition of the donor cells and cultivation conditions.

Also the successful transformation of cereal species has already been described, e.g. for barley (Wan and Lexaux, supra; Ritala et al., supra) and for wheat (Nehra et al. (1994) Plant J. 5, 285–297; Altpeter et al. supra).

Once the introduced DNA is integrated into the genome of the plant cell, it remains stable and is also stably inherited to the progeny of the originally transformed cell. Normally, it contains a selection marker conferring resistance against a biocide or antibiotic such as kanamycin G418, bleomycin, hygromycin, methotrexate, glyphosate, streptomycin, sulfonyl urea, gentamycin or phosphinotricin etc. The selection marker which can be chosen individually should therefore allow selection of transformed cells over cells which are devoid of the introduced DNA.

The transformed cells grow within the plant in the usual manner (see also McCormick et al. (1986) Plant Cell Reports 5, 81–84). The resulting plants can be cultivated in the usual fashion and may be propagated by self-fertilisation or be crossed with plants having the same transformed or other genetic traits. The resulting hybrid individual plants have the respective phenotypic properties. Usually, seeds can be obtained from the plants.

Two or more generations should be grown in order to ensure that the phenotypic trait is stably maintained and inherited. Seeds should also be harvested in order to ensure that the respective phenotype or other characteristics are maintained.

By applying the usual methods, also transgenic lines can be determined, which are homozygous for the new nucleic acid molecules and, their phenotypic behaviour can be examined with respect to altered tocopherol content and compared to that of hemizygous lines.

Expression of the proteins according to the invention having geranylgeranyl reductase activity can be achieved by means of conventional molecular biological and biochemical methods. The skilled person is familiar with these techniques and he is able without any difficulty to choose a suitable detection method, for example, a Northern blot analysis for the detection of geranylgeranyl reductase-specific RNA and for determining the amount of geranylgeranyl reductase-specific RNA accumulation, a Southern blot analysis for the identification of DNA sequences coding for geranylgeranyl reductase or a Western blot analysis for detecting the protein, encoded by the DNA sequences according to the invention, preferably CHL P. Enzymatic activity of geranylgeranyl reductase may, for example, be detected and examined by an enzyme assay, described by Soll and Schultz (1981) in Biochem. Biophys. Res. Commun. 99, 907–912, which is based on the formation of chlorophyll phytyl.

The invention is based on the successful isolation of a cDNA clone coding for geranylgeranyl reductase from a cDNA library from *Nicotiana tabacum* cv. Petit Havana SR1. The sequence of this cDNA clone, which comprises a complete open reading frame, is shown in SEQ ID NO:1. Using the sequence according to SEQ ID NO:1 it was possible to produce transgenic plants which exhibit an altered tocopherol content in comparison to wild-type plants.

The cDNA clone, containing the DNA sequence according to SEQ ID NO:1 was transformed into *Escherichia coli* and the resulting *E. coli* strain was deposited at the Deutsche Sammlung für Mikroorganismen und Zellkulturen GmbH (DSMZ), Mascheroder Weg 1b, D-38124 Braunschweig, Germany under Deposit Number DSM 11816 on Oct. 16, 1997, in accordance with the Budapest Treaty.

The following examples serve the purpose of illustrating the invention.

EXAMPLES

Example 1

Cloning a tobacco cDNA which codes for a geranylgeranyl reductase (CHL P)

For the identification of a geranylgeranyl reductase cDNA from tobacco a Lambda ZAP II cDNA library (*Nicotiana tabacum* SR1, Stratagene, USA) was screened according to the manufacturer's protocol, by using an EST from *Arabidopsis thaliana* which codes for the locus 4D9T7P. The used EST sequence shows similarity to the known bch P/chl P sequences from *Rhodobacter capsulatus* (Young et al. (1989) Mol. Gen. Genet. 218, 1–12; Bollivar et al. (1994) J. Mol. Biol. 237, 622–640; Bollivar et al. (1994) Biochemistry 33, 12763–12768) und Synechocystis PCC6803 (Addlesee et al. (1996) FEBS Lett. 389, 126–130).

The used hybridisation probe comprises the region of the EST sequence in 4D9T7P (Accession No. T04791) from base 1 to base 364. The probe was isolated from the PRL2 library from *A. thaliana* (vector: λZipLox) (Newman et al. (1994) Plant Physiol. 106:1241–1255) as NotI/SalI restriction fragment, and radioactively labelled with [α-$^{32}$P]dCTP by nick translation (Life Technologies, Eggenstein, Germany).

Hybridisation was carried out according to the following protocol:

2 hrs prehybridisation at 55° C. with hybridisation solution having the following composition: 5×SSC, 0.1% SDS, 5×Denhardt reagent, 100 μm/ml denatured salmon sperm DNA;

12 hrs main hybridisation at 55° C. with fresh hybridisation solution having the above composition plus radioactively labelled probe;

Washes:

2 times 10 min. at 55° C. with 2×SSC and 0.1% SDS, and 1 time 5 min. at 55° C. with 1×SSC and 0.1% SDS.

The plasmid DNA, isolated by cDNA library screening, was sequenced by conventional methods. The identified chl P cDNA sequence, shown in SEQ ID NO:1, comprises 1510 nucleotides (without polyA-tail); nucleotides 1 to 1392 encode a 52 kDa protein consisting of 464 amino acid residues (including the start codon methionine, and without the stop codon (nucleotides 1393 to 1395)). The deduced amino acid sequence of the CHL P protein is shown in SEQ ID NO:2. The nucleotide sequence shown in SEQ ID NO:1 comprises a 3' untranslated region from nucleotide 1396 to 1510.

For DNA, RNA isolation, sequence analysis, restriction, cloning, gel electrophoresis, radioactive labelling, Southern, Northern and Western Blot analysis, hybridisation and similar procedures conventional methods were employed, as described in standard laboratory manuals, such as Sambrook et al. (1989) Molecular Cloning: A Laboratory Manual, 2nd Edition, Cold Spring Harbor Laboratory Press, Cold Spring Harbor, N.Y.

Example 2

Transformation of tobacco plants and regeneration of intact plants

For the production of transgenic plants which overexpress CHL P and which, thus, exhibit an increased tocopherol content in comparison to non-transformed plants, the DNA sequence according to SEQ ID NO:1 was cut out of the vector with the restriction enzymes BamHI and SalI, located in the multiple cloning site of the pBluescript vector, and ligated in sense orientation behind the CaMV 35S promoter into the binary vector BinAR-TX (Höfgen and Willmitzer (1990) Plant Science 66, 221–230), a pBIB derivative (Becker (1990) Nucleic Acid Res. 18, 203), digested with the same restriction endonucleases. For the purpose of illustration, a restriction map of the vector BinAR-TX is enclosed as FIG. 3.

Instead of the mentioned binary vector BinAR-TX, any other vector suitable for plant transformation can be used for constructing a chimeric gene, comprising a fusion of the CaMV 35S promoter or any other promoter which provides transcription and translation in plant cells, and DNA sequences which code for CHL P.

The recombinant vector pCHLPbin was then introduced into *Agrobacterium tumefaciens* (strain GV2260; (Horsch et al. (1985) Science 227, 1229–1231) and used for the transformation of tobacco plants (SNN) via the leaf disc transformation technique (Horsch et al., supra).

For this purpose an overnight culture of the resulting *Agrobacterium tumefaciens* clone was centrifuged for 10 minutes at 5000 rpm, and the bacteria were resuspended in 2YT-medium. Young tobacco leaves of a sterile culture (*Nicotiana tabacum* cv. Samsun NN) were cut into small slices of about 1 cm in diameter and incubated for a short period of time in the bacteria suspension. Subsequently, the leaf slices were placed on MS medium (Murashige and Skoog (1962) Physiol. Plant 15, 473; 0.7% Agar), and kept in the dark for two days. Then, the leaf slices were placed on MS medium (0.7% Agar) with 1.6% glucose, 1 mg/l benzylaminopurine, 0.2 mg/l naphthyl acidic acid, 500 mg/l claforan (cefotaxime, Hoechst, Franfurt, Germany) and 50 mg/l kanamycin, for shoot induction. The medium was changed every seven to ten days. After the development of shoots, the leaf slices were transferred into glass vessels, containing the same medium. Developing choots were cut off and placed on MS medium with 2% saccharose and 250 mg/l claforan, and regerated to whole plants.

Example 3

Analysis of transgenic tobacco plants containing the recombinant vector pCHLPbin Transgenic tobacco plants were transformed, selected and regenerated, as described above. After root growth in sterile culture about 100 independent primary transformants were transferred to soil in the green house. The tobacco plants were kept in the green house at 60% humidity and 20–25° C. for 16 hours at light and 18–20° C. for 8 hours in the dark.

The transformants with normal or increased tocopherol and/or chlorophyll contents showed neither abnormal appearance or habitus nor an altered growth rate in comparison to control plants.

Several of the primary transformants showed an up to 4 times to 6 times increased tocopherol content in comparison to wild-type plants. This increase in tocopherol content could be further raised in the progeny of the T1 and T2 generation and in homozygous progeny plants, obtained by usual self-fertilisation and subsequent determination of the segregation pattern of the seeds on kanamycin-containing medium.

Furthermore, it could be observed that the tocopherol contents in transgenic plants were further increased under stress conditions, such as found during the cultivation at low or increased temperatures or under high power light, as well as in senescent leaves, as compared to control plants.

Tocopherol was measured according to the following method:
Leaf discs were homogenised in liquid nitrogen and extracted three times in methanol. The extracts were collected and eluted on a LiCrospher 100 HPLC RP-18-column (Merck, Darmstadt, Germany) at flow of 1 ml/min with the following gradient: 94% solvent B (100% methanol)/6% solvent A (30% methanol, 10% 0.1 M ammonium acetate, pH 5.1) for 7 min., for further 17 min. 99% solvent B/1% solvent A, then further 26 min. 94% solvent B/6% solvent A.

In an alternative procedure the collected extracts were analysed by means of HPLC in a isocratic gradient (gradient as follows: 2% solvent A [10% methanol and 10% acidic acid] and 98% methanol (solvent B); flow rate 1 ml/min). For detection, a Waters LC-module-device with Shimadzu RF 551 fluorescence detector (295 nmex, 325 nmem) was used.

The results of a tocopherol assay are shown in a bar graph in FIG. 4. The comparison of leaves 6, 9, 12 (numbering starting from the top of the plant) of the transformants 28 and 30 with the corresponding leaves of the control plant (SNN) demonstrates that the transgenic lines have a tocopherol content which is up to 6 times higher, compared to wild-type plants.

Irrespective of their ability to grow on kanamycin-containing medium, the transgenic tobacco plants were also analysed by Southern blot hybridisation. After hybridisation with a labelled cDNA fragment for CHL P, additional radioactively labelled bands could be detected using the genomic DNA of the transformants, digested with restriction enzymes, compared to genomic DNA of control plants.

A Northern blot analysis revealed an increased amount of specific RNA in the transformants, compared to the CHL P-RNA contents in control plants.

Further, an increased geranylgeranyl reductase expression could be determined in transgenic plants by Western blot analysis. The transformants showed an increased amount of CHL P protein in comparison to control plants.

Moreover, it could be confirmed by plastid import experiments (carried out according to Grimm et al. (1989) Plant Mol. Biol. 13, 583–593) that the CHL P pre-protein, encoded by the sequence according to SEQ ID NO:1, was imported into the plastides after in vitro transcription and translation.

Example 4

Construction of CHL P antisense constructs and transfer to tobacco

While the transgenic plants produced and analysed according to Examples 2 and 3 exhibit an increased tocopherol content due to overexpression of the DNA sequence according to the invention, the following antisense construct was constructed and transferred to tobacco in order to produce transgenic tobacco plants having reduced CHL P activity.

The cDNA sequence according to SEQ ID NO:1 was cut out of the vector using the restriction enzymes KpnI and XbaI, located in the multiple cloning site of the pBluescript vector, and fused with the 35S promoter of cauliflower mosaic virus in antisense orientation in the binary vector BinAR-TX (cf. Example 2) digested with the same restriction enzymes. The resulting recombinant vector pCHLPAS-bin was transferred to tobacco via *Agrobacterium tumefaciens*-mediated leaf disc transformation, as described in Example 2. Then, transgenic plants were regenerated. Approximately 100 independent transgenic lines were regenerated and proved for the insertion of copies of the transgene by standard methods, such as Southern blotting.

The transformants showed a growth rate slower than that of control plants, lower pigmentation, reduced CHL P-specific RNA and reduced CHL P protein content, high amount of geranylgeranyl chlorophyll (up to 50% of the total chlorophyll content, in comparison to 100% of phytyl chlorophyll in wild-type plants) as well as a reduced chlorophyll and tocopherol content.

Example 5

Over expression of active geranylgeranyl reductase in *Escherichia coli*

For the production of expression clones which overexpress the recombinant CHL P in *E. coli,* the open reading frame for a putatively mature (processed) protein was amplified from the DNA sequence according to SEQ:ID NO. 1 by PCR (1 min 94° C.; 2 min 60° C.; 3 min 72° C.; 25 cycles) using the oligonucleotid primers CSYN 1 (SEQ ID NO:3) 5'-cgc cat ggg ccg caa tct tcg tgt tgc ggt-3' and

CSYN 2 (SEQ ID NO:4) 5'-gca gat ctg tcc att tcc ctt ctt agt gca-3'

The amplified PCR fragment was purified and digested with the restriction enzymes NcoI and BglII, and ligated into the expression vector pQE60 (Qiagen, Hilden, Germany), cut with the same enzymes. The initiation codon ATG (forming part of the recognition sequence for restriction enzyme NcoI) was followed by the chl P sequence, starting with nucleotide 148 of the open reading frame of the CHL P cDNA sequence. As a consequence, the methionine is followed by a glycine, corresponding to amino acid residue 50 of the peptide sequence deduced from the cDNA sequence.

For expression of the plant CHL P, E. coli strains XL 1 Blue (Stratagene, LaJolla, Calif., USA) or SG 13009 (Gottesmann et al. (1981) J. Bacteriol. 148, 256–273) were transformed with the recombinant vector. After induction of transcription of the recombinant gene by addition of IPTG (a protein having a molecular weight of approximately 47 kDa was expressed in the E. coli strains. The protein could be detected in the pellet fraction of the bacterial extract and was purified from the total extract under denaturating conditions using a Ni-affinity column according to manufacturer's instructions (Qiagen, Hilden, Germany).

The purified protein was injected into rabbits for immunisation.

The protein, purified from the total extract, was confirmed to have geranylgeranyl reductase acitivity in a combined enzyme assay with bacterial bacteriochlorophyll synthase by using chlorophyllide and GGPP. The enzyme assay was carried out according to the protocol in Oster et al. (1997) J. Biol. Chem. 272, 9671–9676.

The pigments chlorophyll-GG and chlorophyll-phytol were separated by HPLC on a column (4×250 nm) filled with RP 18 Gromsel 120 ODS5, at 1.2 ml/min flow rate with the following gradient consisting of 60% acetone (solvent A) and 100% acetone (solvent B):$t_0$ 75% solvent A and 25% solvent B, 2 min; within $t_{2-4}$ to 45% solvent A and 55% solvent B; within $t_{4-13}$ to 30% solvent A and 70% solvent B; within $t_{13-17}$ to 100% solvent B; $t_{17-21}$ 100% solvent B isocratic; subsequently within 5 min. to 75% solvent A and 25% solvent B; then further 5 min. 75% solvent A and 25% solvent B isocratic. Tetrapyrroles were detected by use of a fluorescence detector ($\lambda_{ex}$ 425 nm, $\lambda_{em}$ 665 nm).

Example 6

Co-expression of the CHL P gene and the HPD gene in *Nicotiana tabacum*

By use of the oligonucleotid primers hpdoli1 (SEQ ID NO:5) 5'-tta ggt acc atg ggc cac caa acc gcc gcc gtt tca g-3' and hpdoli2 (SEQ ID NO:6) 5'-tga gtc gac cac aat cct tta gtt ggt tct tct tct tg-2'.

the sequence of the HPD cDNA (Accession No.: AF 000228) between nucleotide 37 and 1404 was amplified from an *Arabidopsis thaliana* cDNA library, cloned and sequenced. The amplified fragment was digested with restriction endonucleases KpnI and SalI, and ligated into the binary vector Bin-Hyg-TX, also digested with KpnI and SalI. The vector Bin-Hyg-TX is a pBIB derivative (Becker, supra), as is the vector BinAR-TX, used in Example 2), which enables expression of a coding region, ligated into the multiple cloning site, under control of the 35S RNA promoter of cauliflower mosaic virus. In contrast to the vector Bin-Hyg-TX, used for expression of the CHL P gene, which allows selection in plant cells against kanamycine, the binary vector Bin-Hyg-TX carries a hygromycine resistance gene as the selectable marker for plant cells. For the purpose of illustration, a restriction map of the vector Bin-Hyg-TX is provided in FIG. 5.

Instead of the mentioned binary vector Bin-Hyg-TX any vector suitable for the transformation of plants can be used for constructing a chimeric gene, comprising a fusion of the CaMV 35S promoter or any other promoter, which provides transcription and translation in plant cells, and DNA sequences coding for HPD.

Then, the transfer of the resulting recombinant vector pBinHygHPD onto tobacco SNN was carried out via *Agrobacterium tumefaciens*, as described in the above Example 2, whereby transgenic tobacco shoots were selected on hygromycine-containing medium. Plants obtained after regeneration were used as control plants.

In addition, the transformants 28 and 30, described in Example 2, as well as further transformants, which overexpress the CHL P gene under control of the 35S RNA promoter, were transformed via leaf disc transformation with the recombinant vector pBinHygHPD, and intact plants were regenerated under selection on medium containing both kanamycine and hygromycine.

Successful transfer and expression of the chimeric HPD gene was confirmed in all transgenic plants by suitable Southern and Northern blot hybridisation experiments, using the above-mentioned PCR fragment coding for HPD as the probe.

A comparison of the tocopherol contents (analysis as described in Example 3) in leaves of transgenic plants which only express the CHL P gene (see Example 3, transformants 28 and 30), and plants which co-express the HPD gene and the CHL P gene (transformants 28+HPD and 30+HPD) revealed that the tocopherol content could be further increased by simultaneous expression of the hydroxyphenyl pyruvate dioxygenase gene.

Alternatively transgenic plants which express the CHL P gene as well as the HPD gene can also be obtained by crossing suitable transgenic lines, particularly crossing homozygous "CHL P lines" with homozygous "HPD lines".

An additional increase in tocopherol content can be expected in the double transformants (and double crosses) under stress conditions (e.g. increased temperatures, light stress and the like).

Apart from the above-described double transformants, which express HPD and CHL P, also transgenic HPD lines were analysed with respect to tocopherol content and the influene of stress conditions on their tocopherol content. It could be demonstrated that over-expression of HPD in tobacco leaves results in a 2- to 3-fold increase in tocopherol content, and that the tocopherol content is particularly increased under stress conditions, compared to non-transgenic control plants.

FIG. 6 shows tocopherol contents in the leaves 4, 7 and 10 of 12-week old transgenic tobacco lines (# 2, 6 and 33) which express the Arabidopsis enzyme hydroxyphenyl pyruvate dioxygenase (HPD), in comparison to control plants (SNN). The plants were cultivated either at 38° C. or at 10° C., and a light intensity of approximately 200 $\mu$mol photon/$m^2$/s. Tocopherol is increasingly accumulated in the plants with increasing leaf age. Particularly in older leaves, the tocopherol content increases much more in the plants cultivated at 38° C., and reaches a 2 times higher amount in comparison to control plants. In comparison, the tocopherol contents in the transformants kept at low temperature was only slightly increased in comparison to wild-type plants.

These results indicate that in the case of an increased need for tocopherol, e.g. particularly under stress conditions, HPD specially favours the generation of these antioxidants in transgenic plants.

Example 7

Increased resistance of the transgenic plants against oxidative stress

Transgenic plants produced according to Examples 2 and 3 were analysed in leaf disc incubation experiments with respect to the influence of inhibitory and oxidative substances. 15 seedlings were incubated in 20 mM potassium phosphate buffer (pH 7.1) for 10 hrs in light. Plants were incubated in control samples (water), in samples with 3.3 µM (low concentration=LC) or 33 µM (high concentration=HC) Acifluorfen (available from BASF, Ludwigshafen, Germany), an inhibitor of protoporphyrinogen oxidase, and in samples with 1.7 µM (low concentration=LC) or 17 µM (high concentration=LC) Rose Bengal (acid red, 4,5,6,7-tetrachloro-2',4',5',7'-tetraiodofluorescein, available from Sigma-Aldrich, Deisenhofen, Germany), which produces reactive oxygen species. The content of tocopherol is about 2 to 3 times higher in the analysed transgenic lines (28, 30) in the buffer control samples as well as under oxidative stress conditions, compared to wild-type plants (SNN). The results are given in FIG. 7.

The results indicate that due to their increased tocopherol content, as compared to wild-type plants, the plants according to the invention exhibit increased tolerance against oxidative stress. Therefore, an increased antioxidative protection of cellular membranes against reactive oxygen species can be expected in the plants according to the invention.

Example 8

Tocopherol content in seeds of transgenic plants

Tocopherol was extracted according to the above-described procedure from seeds of transgenic plants which exhibit an increased tocopherol content in leaves compared to wild-type plants due to the expression of CHL P under control of the CaMV 35S promoter (see Example 2). The results of the tocopherol quantification by means of HPLC are shown in FIG. 8, in comparison to tobacco control plants.

Besides α-tocopherol also γ-tocopherol was quantified. The latter is generally present in tobacco seeds in higher amounts; the ratio of γ-tocopherol to α-tocopherol is about 10:1 in tobacco seeds. The contents of both forms of tocopherol, particularly α-tocopherol, are 2- to 3-times higher in transgenic plants having increased geranylgeranyl reductase expression, in comparison to control plants.

These results which reflect the impact of constitutive CHL P expression under control of the 35S promoter on the tocopherol content in seed, clearly indicate that by use of a seed-specific promoter (or a promoter which is specifically inducible in seed tissue) expression of geranylgeranyl reductase in seed tissue and as a consequence the tocopherol content in seeds of transgenic plants can be further increased.

Should a molecular biological procedure in any way not have been adequately described, it was carried out following standard methods, as described, for example, by Sambrook et al. (1989) Molecular Cloning: A Laboratory Manual, 2nd Edition, Cold Spring Harbor Press, Cold Spring Harbor, N.Y. With respect to the transformation of plants it is referred to generally known review articles as well as the reports and publications mentioned herein.

Description of the Figures

FIG. 1: SEQ ID NO:1 shows a nucleotide sequence of the chl P cDNA of geranylgeranyl reductase (CHL P) from *Nicotiana tabacum.*

FIG. 2: SEQ ID NO:2 shows an amino acid sequence of the enzyme CHL P from *N. tabacum,* deduced from the SEQ ID NO:1 shown in FIG. 1

FIG. 6: Bar diagram of the tocopherol contents in the leaves 4, 7 and 10 in 12-weeks old transgenic lines (# 2, 6, 33), which express the Arabidopsis enzyme HPD, and in control plants (SNN).

SEQUENCE LISTING

<160> NUMBER OF SEQ ID NOS: 6

Figure 3:
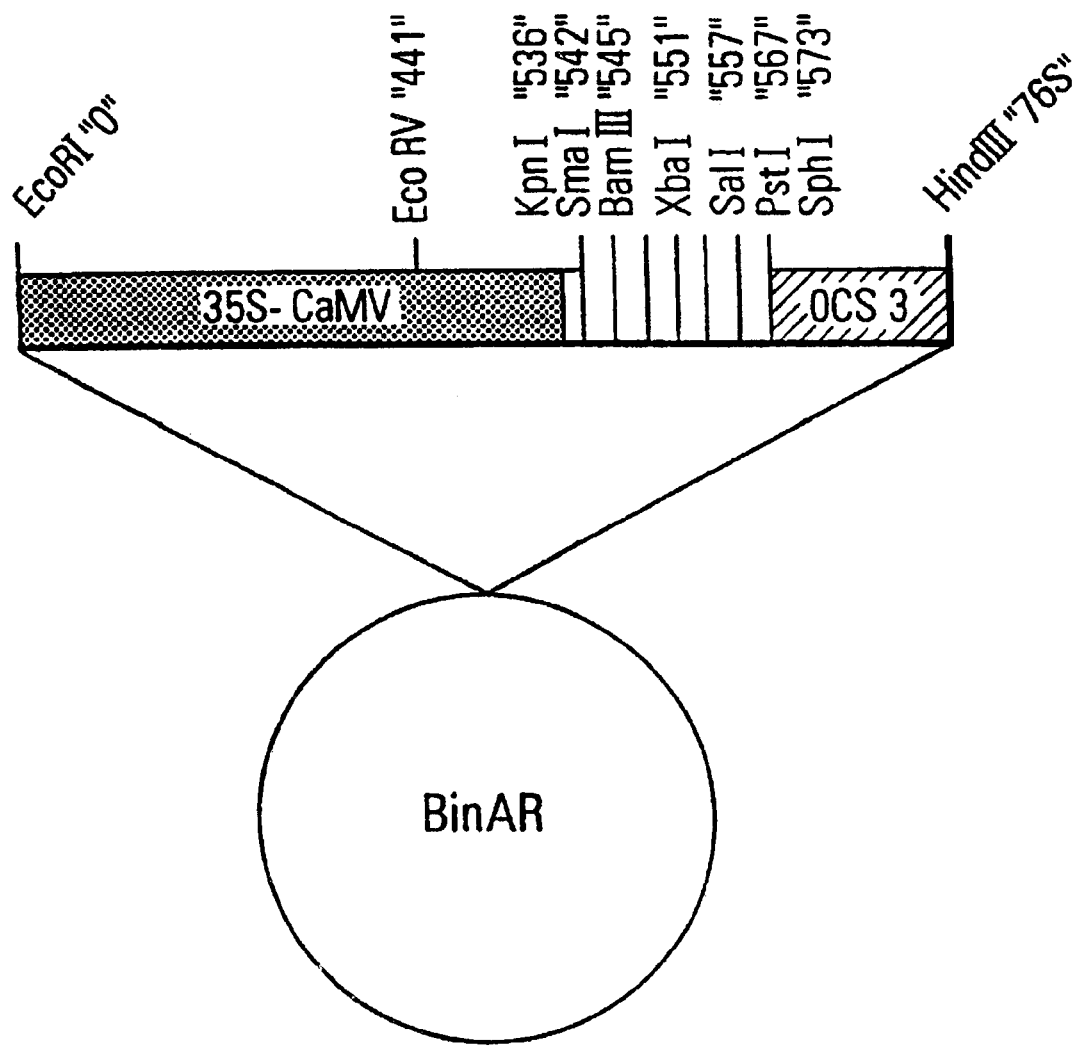
FIG. 3: Restriction map of the binary vector BinAR, as used in plant transformation experiments. BinAR (Höfgen and Willmitzer (1990) Plant Science 66, 221) is a Bin19 derivative (Bevan (1984) Nucl. Acids Res. 12, 8711), which contains an expression cassette for the constitutive expression of chimeric genes in plants, the expression cassette being cloned via the EcoRI and HindIII restriction sites of Bin19. The cassette comprises a 770 base pair EcoRI/HindIII fragment, containing the CaMV 35S promoter, part of the pUC18 polylinker as well as the termination signal of the octopine synthase gene (OCS). For insertion of coding sequences the unique restriction sites of the pUC18 polylinker, i.e. KpnI, SmaI, BamHI, XbaI and SalI are particularly useful. As plant selection marker, the binary vector BinAR carries a kanamycine resistance gene.
Figure 4:
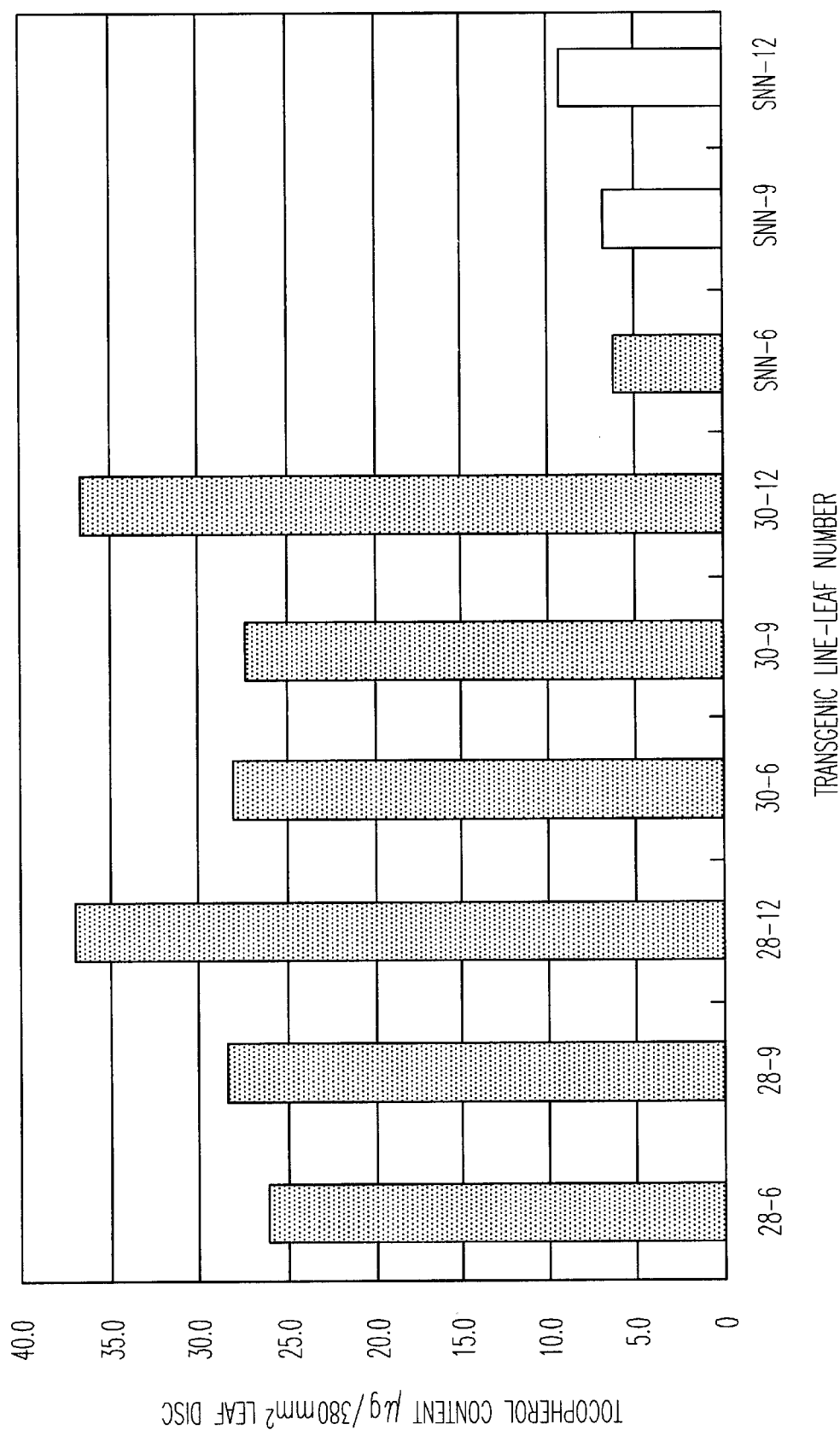
FIG. 4: Bar diagram showing the tocopherol content in the leaves 6, 9, 12 (numbering starting from the top of the plant) of transgenic tobacco plants (lines 28 and 30) versus the corresponding leaves of control plants (SNN).
Figure 5:
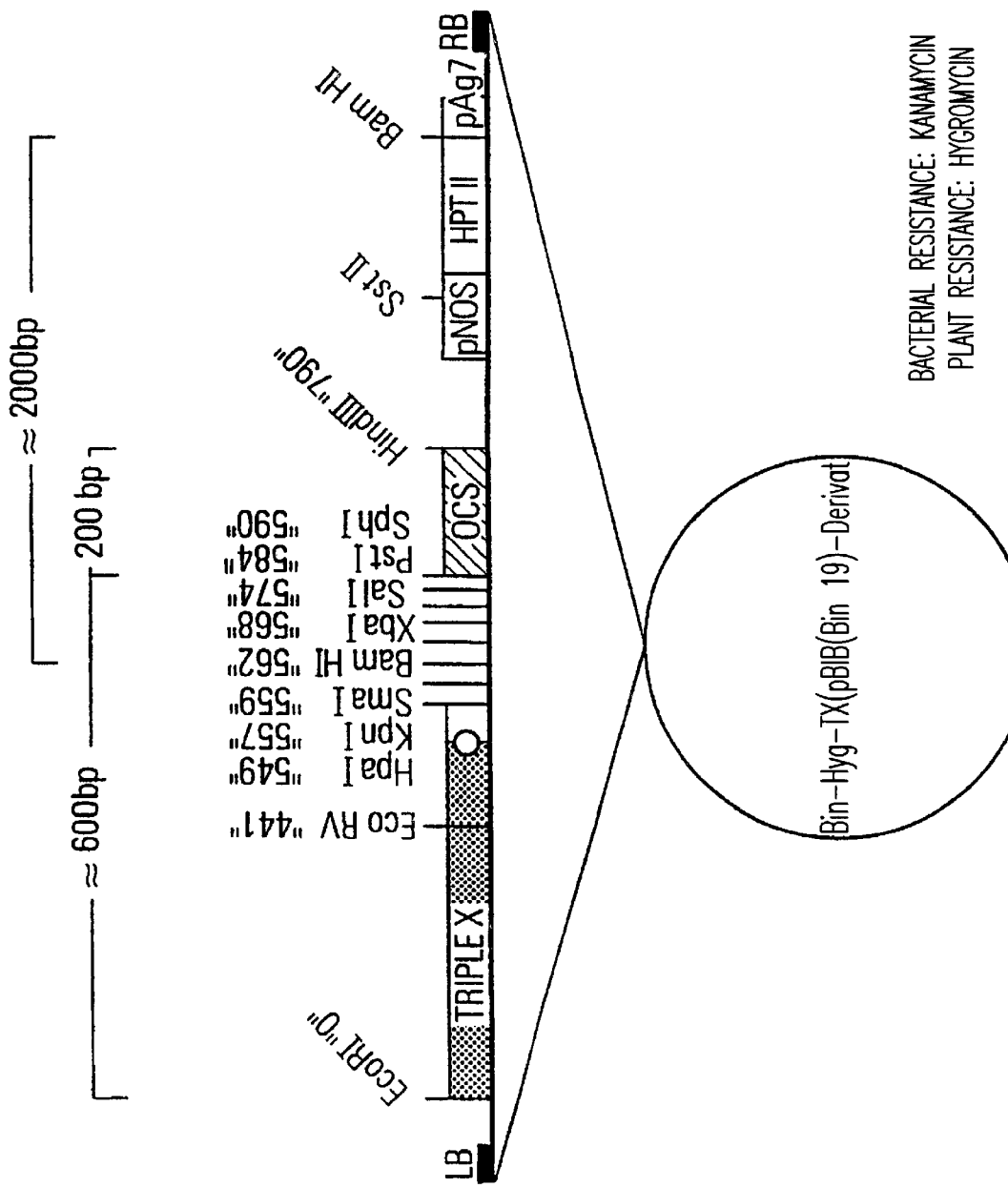
FIG. 5: Restriction map of the binary vector Bin-Hyg-TX, as used for plant transformation, which is also a pBIB-derivative (Becker, supra; Bevan, supra), containing an expression cassette for the constitutive expression of chimeric genes in plants. For insertion of coding sequences the unique restriction sites of the pUC18 polylinker, i.e. HpaI, KpnI, SmaI, XbaI and SalI are especially useful. As the plant selection marker, the binary vector Bin-Hyg-TX carries a hygromycine resistance gene.
Figure 7:
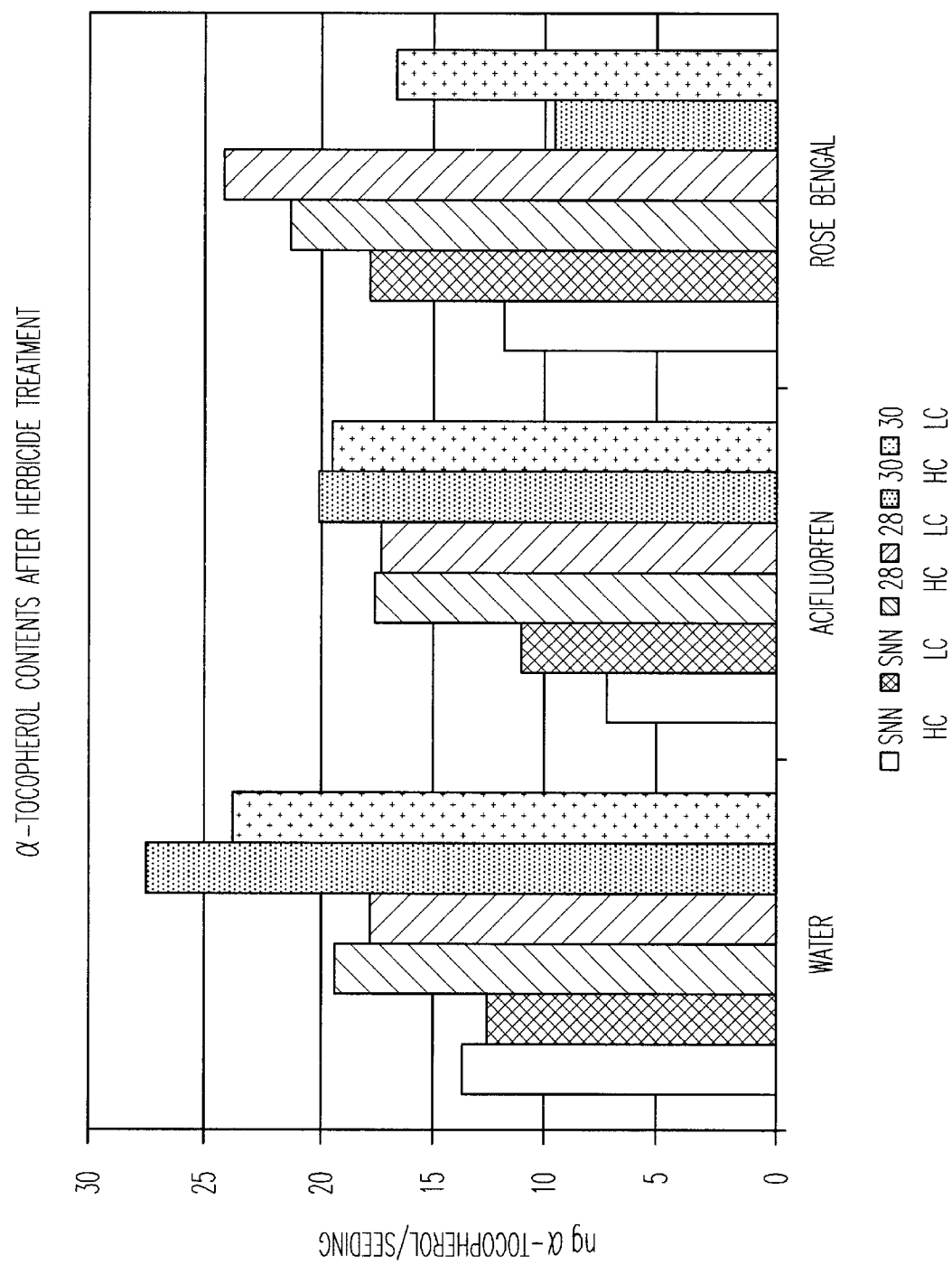
FIG. 7: Tocopherol content in 12-days old seedlings, incubated for 10 hrs at light in 20 mM potassium phosphate buffer (pH 7.1; control=water), with 3.3 µM (LC) or 33 µM (HC) Acifluorfen, and with 1.7 µM (LC) or 17 µM (HC) Rose Bengal (SNN=wild-type control plants, 28 and 39=transgenic lines).
Figure 8:
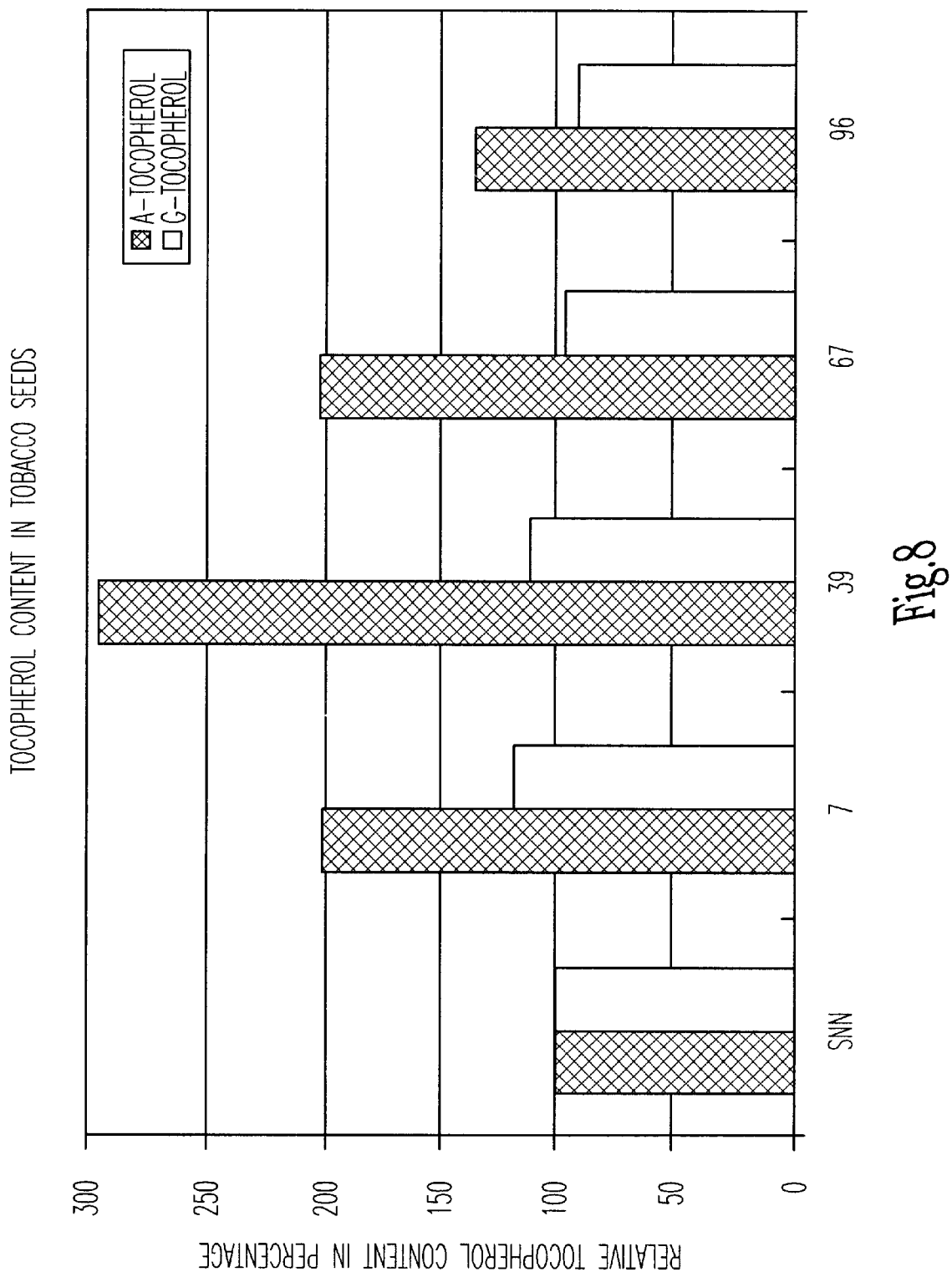
FIG. 8: Relative α-tocopherol and γ-tocopherol values in seeds of transgenic tobacco plants (# 7, 39, 67, 96) and wild-type tobacco plants (SNN). 100% α-tocopherol corresponds to 6 ng/mg seeds; 100% γ-tocopherol corresponds to 62.8 ng/mg seeds.

<210> SEQ ID NO 1
<211> LENGTH: 1510
<212> TYPE: DNA
<213> ORGANISM: Nicotiana tabacum

<400> SEQUENCE: 1

| | | | | | |
|---|---|---|---|---|---|
| atggcttcca | ttgctctcaa | aactttcacc | ggcctccgtc | aatcctcgcc | ggaaaacaat | 60 |
| tccattactc | tttctaaatc | cctccccttc | acccaaaccc | accgtaggct | ccgaatcaat | 120 |
| gcttccaaat | ccagcccaag | agtcaacggc | cgcaatcttc | gtgttgcggt | ggtgggcggt | 180 |
| ggtcctgctg | gtggcgccgc | cgctgaaaca | ctcgccaagg | gaggaattga | aaccttctta | 240 |
| atcgaacgca | aaatggacaa | ctgcaaaccc | tgcggtgggg | ccatcccact | ttgcatggtg | 300 |
| ggagaatttg | acctcccttt | ggatatcatt | gaccggaaag | ttacaaagat | gaagatgatt | 360 |
| tccccatcca | acgttgctgt | tgatattggt | cagactttaa | agcctcacga | gtacatcggt | 420 |
| atggtgcgcc | gcgaagtact | cgatgcttac | ctccgtgacc | gcgctgctga | agccggagcc | 480 |
| tctgttctca | acggcttgtt | cctcaaaatg | gacatgccca | agctcccaa | cgcaccttac | 540 |
| gtccttcact | acacagctta | cgactccaaa | actaatggcg | cggggagaa | gcgtaccctg | 600 |
| gaagttgacg | ccgttatcgg | cgctgacggt | gcaaattccc | gtgtcgcaaa | atccataaac | 660 |
| gccggtgact | acgagtacgc | tattgcattc | caagaaagga | ttaaaatttc | cgatgataaa | 720 |
| atgaagtatt | acgagaattt | agctgaaatg | tacgtgggtg | atgacgtgtc | ccctgatttt | 780 |
| tacgggtggg | ttttccccaa | atgtgaccac | gttgccgttg | gcactggcac | agtcaccac | 840 |
| aaagctgaca | tcaaaaaatt | ccagctagct | acaagattga | gagctgattc | caaaatcacc | 900 |
| ggcgaaaaa | ttatccgggt | cgaggcccac | ccgattccag | aacacccaag | acccagaaga | 960 |
| ttacaagaca | gagttgcatt | ggttggtgat | gcggcagggt | acgtgaccaa | atgttcgggc | 1020 |
| gaagggatt | acttcgcggc | aaagagtgga | cgtatgtgtg | ctgaagcaat | tgttgaaggg | 1080 |
| tcagaaatgg | gaaaaagaat | ggtggacgag | agtgatttga | ggaagtattt | ggagaaatgg | 1140 |
| gacaagactt | attggccaac | gtacaaggtg | cttgatatat | tgcagaaggt | attttacagg | 1200 |
| tcgaatccgg | cgagggaagc | atttgttgaa | atgtgcgcag | atgagtatgt | gcagaagatg | 1260 |
| acatttgaca | gctatttgta | caagaaagta | gcaccaggaa | acccaattga | agacttgaag | 1320 |
| cttgctgtga | ataccattgg | aagtttggtg | agagctaatg | cactaagaag | ggaaatggac | 1380 |
| aagctcagtg | tataagaaga | ttaacagcat | taatattttc | ttgtaattga | aggatttatt | 1440 |
| tctcaaatta | ctctgtaaac | acctttcatc | ctgcctttaa | tcggatttat | gtaacttcat | 1500 |
| aatttgagct | | | | | | 1510 |

<210> SEQ ID NO 2
<211> LENGTH: 464
<212> TYPE: PRT
<213> ORGANISM: Nicotiana tabacum

<400> SEQUENCE: 2

Met Ala Ser Ile Ala Leu Lys Thr Phe Thr Gly Leu Arg Gln Ser Ser
 1               5                  10                  15

Pro Glu Asn Asn Ser Ile Thr Leu Ser Lys Ser Leu Pro Phe Thr Gln
            20                  25                  30

-continued

```
Thr His Arg Arg Leu Arg Ile Asn Ala Ser Lys Ser Pro Arg Val
     35                  40                  45

Asn Gly Arg Asn Leu Arg Val Ala Val Val Gly Gly Pro Ala Gly
     50                  55                  60

Gly Ala Ala Ala Glu Thr Leu Ala Lys Gly Gly Ile Glu Thr Phe Leu
65                   70                  75                  80

Ile Glu Arg Lys Met Asp Asn Cys Lys Pro Cys Gly Gly Ala Ile Pro
                 85                  90                  95

Leu Cys Met Val Gly Glu Phe Asp Leu Pro Leu Asp Ile Ile Asp Arg
                100                 105                 110

Lys Val Thr Lys Met Lys Met Ile Ser Pro Ser Asn Val Ala Val Asp
                115                 120                 125

Ile Gly Gln Thr Leu Lys Pro His Glu Tyr Ile Gly Met Val Arg Arg
    130                 135                 140

Glu Val Leu Asp Ala Tyr Leu Arg Asp Arg Ala Ala Glu Ala Gly Ala
145                 150                 155                 160

Ser Val Leu Asn Gly Leu Phe Leu Lys Met Asp Met Pro Lys Ala Pro
                165                 170                 175

Asn Ala Pro Tyr Val Leu His Tyr Thr Ala Tyr Asp Ser Lys Thr Asn
                180                 185                 190

Gly Ala Gly Glu Lys Arg Thr Leu Glu Val Asp Ala Val Ile Gly Ala
        195                 200                 205

Asp Gly Ala Asn Ser Arg Val Ala Lys Ser Ile Asn Ala Gly Asp Tyr
    210                 215                 220

Glu Tyr Ala Ile Ala Phe Gln Glu Arg Ile Lys Ile Ser Asp Asp Lys
225                 230                 235                 240

Met Lys Tyr Tyr Glu Asn Leu Ala Glu Met Tyr Val Gly Asp Asp Val
                245                 250                 255

Ser Pro Asp Phe Tyr Gly Trp Val Phe Pro Lys Cys Asp His Val Ala
                260                 265                 270

Val Gly Thr Gly Thr Val Thr His Lys Ala Asp Ile Lys Lys Phe Gln
        275                 280                 285

Leu Ala Thr Arg Leu Arg Ala Asp Ser Lys Ile Thr Gly Gly Lys Ile
    290                 295                 300

Ile Arg Val Glu Ala His Pro Ile Pro Glu His Pro Arg Pro Arg Arg
305                 310                 315                 320

Leu Gln Asp Arg Val Ala Leu Val Gly Asp Ala Ala Gly Tyr Val Thr
                325                 330                 335

Lys Cys Ser Gly Glu Gly Ile Tyr Phe Ala Ala Lys Ser Gly Arg Met
                340                 345                 350

Cys Ala Glu Ala Ile Val Glu Gly Ser Glu Met Gly Lys Arg Met Val
        355                 360                 365

Asp Glu Ser Asp Leu Arg Lys Tyr Leu Glu Lys Trp Asp Lys Thr Tyr
    370                 375                 380

Trp Pro Thr Tyr Lys Val Leu Asp Ile Leu Gln Lys Val Phe Tyr Arg
385                 390                 395                 400

Ser Asn Pro Ala Arg Glu Ala Phe Val Glu Met Cys Ala Asp Glu Tyr
                405                 410                 415

Val Gln Lys Met Thr Phe Asp Ser Tyr Leu Tyr Lys Lys Val Ala Pro
                420                 425                 430

Gly Asn Pro Ile Glu Asp Leu Lys Leu Ala Val Asn Thr Ile Gly Ser
        435                 440                 445
```

```
Leu Val Arg Ala Asn Ala Leu Arg Arg Glu Met Asp Lys Leu Ser Val
    450                 455                 460

<210> SEQ ID NO 3
<211> LENGTH: 30
<212> TYPE: DNA
<213> ORGANISM: Artificial Sequence
<220> FEATURE:
<223> OTHER INFORMATION: A primer

<400> SEQUENCE: 3
cgccatgggc cgcaatcttc gtgttgcggt                                    30

<210> SEQ ID NO 4
<211> LENGTH: 30
<212> TYPE: DNA
<213> ORGANISM: Artificial Sequence
<220> FEATURE:
<223> OTHER INFORMATION: A primer

<400> SEQUENCE: 4
gcagatctgt ccatttccct tcttagtgca                                    30

<210> SEQ ID NO 5
<211> LENGTH: 36
<212> TYPE: DNA
<213> ORGANISM: Artificial Sequence
<220> FEATURE:
<223> OTHER INFORMATION: A primer

<400> SEQUENCE: 5
ttaggtacca tgggccacca aaccgccgcc gtttca                             36

<210> SEQ ID NO 6
<211> LENGTH: 38
<212> TYPE: DNA
<213> ORGANISM: Artificial Sequence
<220> FEATURE:
<223> OTHER INFORMATION: A primer

<400> SEQUENCE: 6
tgagtcgacc acaatccttt agttggttct tcttcttg                           38
```

What is claimed is:

1. A transgenic plant transformed with a nucleic acid sequence encoding the protein of SEQ ID NO:2, wherein the protein has the activity of a geranylgeranyl reductase, wherein the nucleic acid sequence is transcribed in said transgenic plant.

2. The plant according to claim 1, wherein the protein having the activity of a geranylgeranyl reductase is expressed in the transgenic plant.

3. The plant according to claim 1, which exhibits an increased tocopherol content in comparison to a wild-type plant.

4. The plant according to claim 1, wherein said plant is a dicot.

5. The plant according to claim 4, which is a crop plant, food and/or forage plant, selected from the group consisting of rape, soybean, tomato, potato, sugar beet, and clover.

6. The plant according to claim 1, wherein said plant is a monocot.

7. The plant according to claim 6, which is selected from the group consisting of a crop plant, a forage plant, a cereal plant a wheat, barley, maize, oats, rye, rice, a sweet grass and pasture grass plant.

8. The plant according to claim 1, wherein the nucleic acid sequence is integrated into the plant genome.

9. A transgenic plant cell, which contains an isolated nucleic acid sequence coding for the protein of SEQ ID NO:2 and having the activity of a geranylgeranyl reductase, wherein the nucleic acid sequence is transcribed in the transgenic plant cell.

10. A plant cell according to claim 9, which exhibits an increased tocopherol content in comparison to a non-transformed plant cell.

11. A method for producing a plant or plant cell comprising the following steps:
   a) producing a nucleic acid sequence, comprising the following constituents, fused in 5'-3' orientation:
       a promoter functional in plants, preferably a seed-specific promoter,
       a nucleic acid sequence which codes for the protein of SEQ ID NO:2, wherein the protein has geranylgeranyl reductase activity, and
       optionally, a terminal signal for the termination of transcription and addition of a poly-A-tail to the corresponding transcript, as well as, optionally, DNA sequences deduced therefrom;

b) transferring the nucleic acid sequence from step a) to plant cells and, optionally, integration of the nucleic acid sequence into the plant genome c) if desired, regenerating completely transformed plants, and optionally, propagating the plants.

12. A transgenic plant produced according to the method of claim 11.

13. A method of obtaining tocopherols comprising obtaining the transgenic plant of claim 1 and isolating tocopherols from the transgenic plant.

14. The method of claim 11, wherein the plant or plant cell exhibits an increased tocopherol content.

15. The plant according to claim 1 wherein the nucleic acid sequence encodes a protein from tobacco.

16. The plant according to claim 1 wherein the nucleic acid sequence comprises SEQ ID NO:1.

17. The plant according to claim 1 wherein the nucleic acid sequence further encodes a regulatory element.

18. The plant according to claim 1 wherein the nucleic acid sequence further comprises a promoter.

19. The plant according to claim 18 wherein the promoter is a constitutive promoter.

20. The plant according to claim 18 wherein the promoter is an inducible promoter.

21. The plant according to claim 18 wherein the promoter is a tissue-specific promoter.

22. The plant according to claim 18 wherein the promoter is a developmental specific promoter.

23. The plant according to claim 18 wherein the promoter is a seed-specific promoter.

24. The plant according to claim 1 wherein the nucleic acid sequence further encodes enhancer sequences.

25. The plant according to claim 1 wherein the nucleic acid sequence further encodes signal peptides.

26. The plant according to claim 1 wherein the nucleic acid sequence is in anti-sense orientation.

27. A plant cell of the transgenic plant of claim 1, wherein the plant cell comprises the nucleic acid sequence encoding the protein of SEQ ID NO:2.

28. Progeny of the transgenic plant of claim 1, wherein each of the progeny comprises the nucleic acid sequence encoding the protein of SEQ ID NO:2.

29. A seed produced by the transgenic plant of claim 1, wherein the seed comprises the nucleic acid sequence encoding the protein of SEQ ID NO:2.

30. Transgenic propagation material derived from the plant of claim 1, wherein the material comprises an isolated nucleic acid sequence encoding a protein comprising SEQ ID NO:2.

31. The transgenic propagation material of claim 30, that is a protoplast, a callus, or a cutting.

* * * * *